US006449511B1

(12) United States Patent
Mintchev et al.

(10) Patent No.: US 6,449,511 B1
(45) Date of Patent: Sep. 10, 2002

(54) GASTROINTESTINAL ELECTRICAL STIMULATOR HAVING A VARIABLE ELECTRICAL STIMULUS

(75) Inventors: Martin P. Mintchev; Kenneth L. Bowes, both of Alberta (CA)

(73) Assignee: University Technologies International Inc., Calgary (CA)

( * ) Notice: Subject to any disclaimer, the term of this patent is extended or adjusted under 35 U.S.C. 154(b) by 0 days.

(21) Appl. No.: 09/550,086

(22) Filed: Apr. 14, 2000

Related U.S. Application Data

(63) Continuation-in-part of application No. 09/254,364, filed as application No. PCT/CA97/00616 on Sep. 4, 1997, now Pat. No. 6,243,607.
(60) Provisional application No. 60/025,500, filed on Sep. 5, 1996.

(51) Int. Cl.[7] .................................. A61N 1/36
(52) U.S. Cl. ...................................... 607/40
(58) Field of Search ............................. 607/40, 41, 2, 607/118, 116, 124, 133

(56) References Cited

U.S. PATENT DOCUMENTS

| 3,543,761 A | 12/1970 | Bradley |
| 3,646,940 A | 3/1972 | Timm et al. |
| 3,941,136 A | 3/1976 | Bucalo |
| 4,607,639 A | 8/1986 | Tanagho et al. |
| 5,690,691 A | 11/1997 | Chen et al. |
| 5,836,994 A | 11/1998 | Bourgeois |
| 6,238,423 B1 * | 5/2001 | Bardy ................. 607/40 |
| 6,243,607 B1 * | 6/2001 | Mintchev et al. .......... 607/133 |

FOREIGN PATENT DOCUMENTS

| WO | 9213592 | 8/1992 |
| WO | 9401172 | 1/1994 |

OTHER PUBLICATIONS

Bellahsene, B.E., C.D. Lind, B.D. Schirmer, O.L. Updike, and R.W. McCallum, "Acceleration of gstric emptying with electrical stimulation in a canine model of gastroparesis," *Am. J. Physiol.* 262 (5 Pt 1): G826–34, 1992.

Berger, T., J. Kewenter and N.G. Kock, "Response to Gastrointestinal Pacing: Antral, Duodenal and Jejunal Motility in Control and Postoperative Patients," *Annals of Surgery* 164: 139–44, 1965.

Chen, J.D., B.D. Schirmer, and R.W. McCallum, "Serosal and cutaneous recordings of gastric myoelectrical activity in patients with gastroparesis," *Am J. Physiol.* 266 (1 Pt 1): G90–8, 1994.

(List continued on next page.)

*Primary Examiner*—Kennedy Schaetzle
(74) *Attorney, Agent, or Firm*—Terrence N. Kuharchuk; Rodman & Rodman

(57) ABSTRACT

A device and method for electrical stimulation of a portion of the gastro-intestinal tract, defining a longitudinal axis. A proximal and at least one distal electrode set are arranged circumferentially about the portion of the gastro-intestinal tract in a plane substantially perpendicular to the longitudinal axis and in axially spaced relationship relative to each other. At least one power source provides a variable electrical stimulus to the electrode sets sufficient to stimulate the smooth muscle to produce a local circumferential contraction at each electrode set, wherein the electrical stimulus is variable between each of the proximal and distal electrode sets. A timing mechanism phase locks the electrical stimulus such that it is applied to the electrode sets successively, preferably in an overlapping manner, and repetitively. The axially spaced relationship between the electrode sets and the timing of the electrical stimulus are selected such that the local circumferential contractions are artificially propagated distally through the portion of the gastro-intestinal tract.

76 Claims, 17 Drawing Sheets

OTHER PUBLICATIONS

Daniel, E.E. and S.K. Sarna, "Distribution of Excitory Vagal Fibers in Canine Gastric Wall to Control Motility," *Gastroenterology* 71:608–13, 1976.

Familoni, B.O., T.L. Abell, G. Voeller, A. Salem, O. Gaber, and D. Nemoto, "Long–term electrical stimulation of the human stomach," *Gastroenterology* 106 (2) : A496, 1994.

Familoni, B.O.,T.L. Abell, D. Nemoto, G. Voeller and B. Johnson, Efficacy of electrical stimulation at frequencies higher than basal rate in canine stomach, *Digestive Diseases and Sciences* 42: 892–897, 1997.

Sarna, S.K., K.L. Bowes, and E.E. Daniel, "Gastric Pacemakers," *Gastroenterology* 70: 226–31, 1976.

The GEMS Group, "Electrical stimulation for the treatment of gastroparesis —preliminary report of a multicenter international trial," Abstract from Proceedings of the Fourth International Workshop on Electrogastrography, held May 23, 1996, p. 24.

Familoni, B.,T.Abell, Prem, S. Moolchandani,.G. Voeller, "Optimum Frequency for Stimulating Canine Gastric Electrical Activity," Abstract from Proceedings of the Fourth International Workshop on Electrogastrography, held May 23, 1996, p. 23.

Familoni, B.,T. Abell, S. Bhaskar, G. Voeller, "Evaluation of Gastric Electrical Stimulation in Patients with PEGs," Abstract from Proceedings of the Fourth International Workshop on Electrogastrography, held May 23, 1996, p. 22.

Familoni, B., T. Abell, Z. Gan, G. Voeller, "Computer Simulation for Predicting Efficient Gastric Electricial Stimulation," Abstract from Proceedings of the Fourth International Workshop on Electrogastrography held May 23, 1996, p. 21.

Chen, J.D.Z., Z.Y. Lin, B.D. Schirmer, R.D. Williams, B. Ross and R.W. McCallum, "Effect of gastric pacing with optimal parameters on gastric emptying in patients with gastroparesis," In: Proceedings of XV Int. Sumposium on Gastrointestinal Motility, p. 42. Rome, Italy, Oct. 1995.

Bilgutay, A.M., R. Wingrove, W.O. Griffin, R.C. Bonnabeau and C. W. Lillehei, "Gastro–intestinal Pacing. A New Concept in the Treatment of Ileus," *Ann. Surg.,* 158: 338–48, 1963.

Kelly, K.A. and C.F. Code, Duodenal–gastric reflux and slowed gastric emptying by electrical pacing of the canine duodenal pacesetter potential, *Gastroenterol.,* 72: 429–33, 1977.

Mirrizzi, N., R. Stella, U. Scafoglieri, A Model of extra cellular wave shape of the gastric electricial activity, Med. Biol. Eng. & Comput, 23:33–37, 1985.

Mirrizzi, N., R. Stella, U. Scafoglieri, Model to stimulate the gastric electricial control and response activity on the stomach wall and on abdominal surface, *Med. Biol. Eng. & Comput,* 24: 157–63, 1986.

Mintchev, M.P. and K.L. Bowes, "Conoidal Dipole Model of the Electricial Field Produced by the Human Stomach," *Med. Biol. Eng. & Comput.,* 33:179–85, 1995.

Quast, D.C., A.C. Beall and M.E. DeBakey, "Clinical Evaluation of the Gastrointestinal Pacer," *Surg. Gynec. Obstet.,* 120: 35–37, 1965.

Miedema, B.W., M.G. Sarr and K.A. Kelly, "Pacing the Human Stomach," *Surgery* 111: 143–50, 1992.

Hocking, M.P., S.B. Vogel and C.A. Sininsky, "Human Gastric Myoelectric Activity and Gastric Emptying Following Gastric Surgery and With Pacing," *Gastroenterology* 103: 1811–16, 1992.

Eagon, J.C., and K.A. Kelly, "Effect of electrical stimulation on gastric electrical activity, motility and emptying," *Neurogastroenterology & Motility,* 7:39–45, 1995.

Christensen, J., "Responses of the Smooth Muscle Segment of the Oppossum Esophagus to Distention and Electrical Stimulation, and their Modification by Antagonists," In: Gastrointestinal Motility. International Symposium on Motility of the Gastrointestinal Tract, pp. 167–174, Erlangen, Jul. 15 and 16, 1969.

Mintchev, M.P., Bowes, K.L., "Computer model of gastric electrical stimulation" Ann. Biomed. Eng. 25:726–730, 1997.

McCallum, Richard W., Chen, Jian De Z., Lin, Zhiyue, Schirmer, Bruce D., Williams, Ronald D., and Ross, Robert A., "Gastric Pacing Improves Emptying and Symptoms in Patients with Gastroparesis," *Gastroenterology* 114:456–461, 1998.

Mintchev, Martin P., Otto, Stanislaw J., and Bowes, Kenneth L., "Electrogastrography can Recognize Gastric Electrical Uncoupling in Dogs," *Gastroenterology* 112:2006–2011, 1997.

Familoni, Babajide O., Abell, Thomas L., Voeller, Guy, Salem, Atef and Gaber, Osama, "Electrical Stimulation at a Frequency Higher than Basal Rate in Human Stomach," *Digestive Diseases and Sciences,* 42:885–891.

\* cited by examiner

FIG. 1
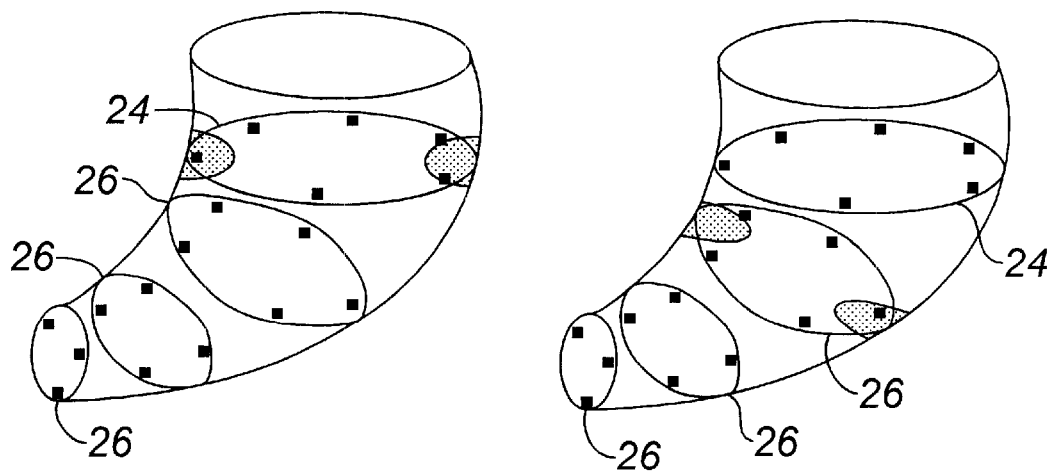
1            2
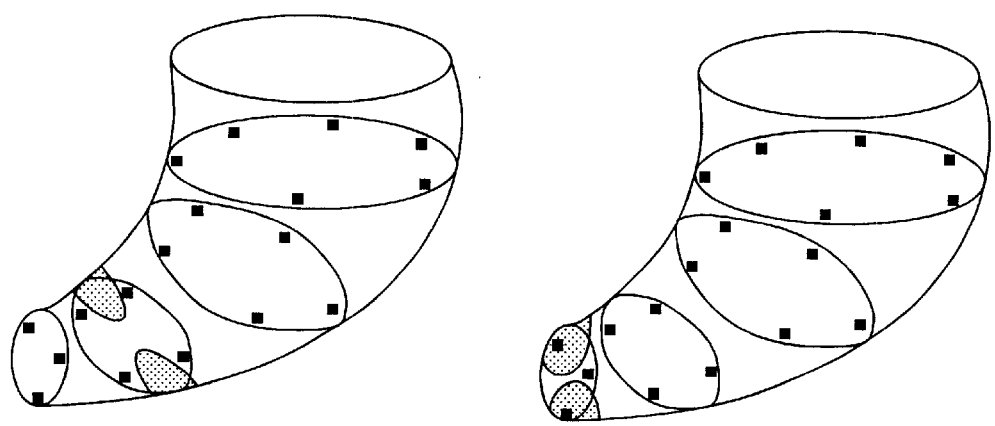
3            4

FIG. 8

|  | SPONTANEOUS EMPTYING T1/2 (AVERAGE±SD) | STIMULATED EMPTYING T1/2 (AVERAGE±SD) |
|---|---|---|
| DOG 1 | 38.6±4.2 MIN. | 2.7±0.4 MIN. |
| DOG 2 | 22.6±3.1 MIN. | 4.0±1.0 MIN. |
| DOG 3 | 48.4±6.8 MIN. | 9.4±1.9 MIN. |
| DOG 4 | 31.3±3.2 MIN. | 4.7±0.3 MIN. |
| DOG 5 | 16.5±18.4 MIN. | 9.3±4.0 MIN. |
| DOG 6 | 13.3±1.2 MIN. | 11.3±7.2 MIN. |
| DOG 7 | 19.3±6.8 MIN. | 6.8±2.3 MIN. |
| DOG 8 | 12.3±5.13 MIN. | 5.6±1.15 MIN. |

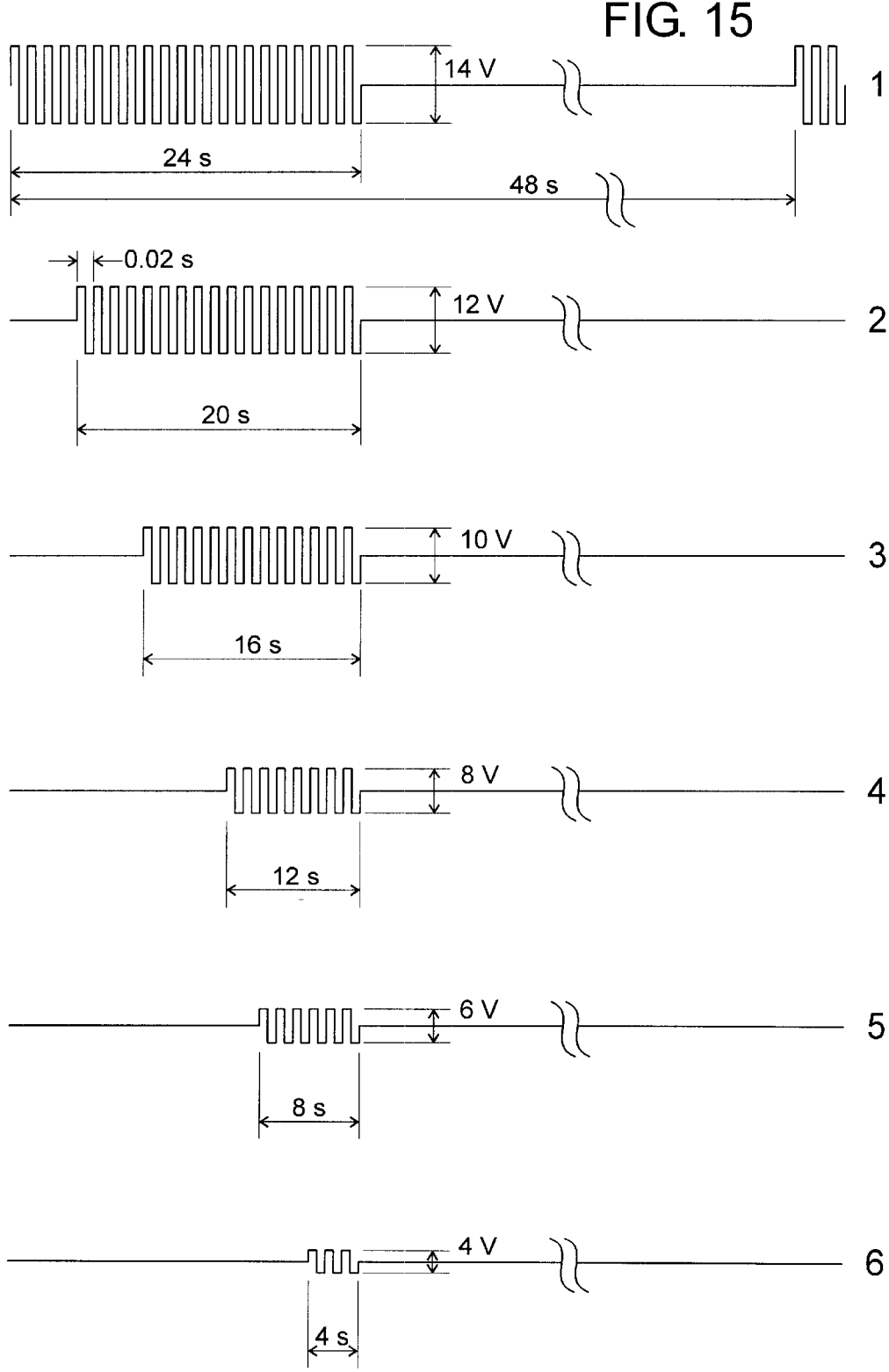

FIG. 16

| DOG AND SESSION NUMBER | NUMBER OF EXPELLED PELLETS | |
|---|---|---|
| | AFTER ½ HOUR OF SPONTANEOUS EMPTYING | AFTER ½ HOUR OF STIMULATED EMPTYING |
| DOG 1, SESSION 1 | 1 | 14 |
| DOG 1, SESSION 2 | 0 | 17 |
| DOG 1, SESSION 3 | 0 | 13 |
| DOG 2, SESSION 1 | 1 | 14 |
| DOG 2, SESSION 2 | 0 | 4 |
| DOG 3, SESSION 1 | 2 | 7 |
| DOG 3, SESSION 2 | 0 | 7 |
| DOG 4, SESSION 1 | 0 | 13 |
| DOG 4, SESSION 2 | 0 | 0 |
| DOG 4, SESSION 3 | 0 | 6 |
| DOG 5, SESSION 1 | 0 | 4 |
| DOG 5, SESSION 2 | 0 | 0 |
| DOG 5, SESSION 3 | 1 | 1 |
| DOG 5, SESSION 4 | 0 | 1 |
| DOG 6, SESSION 1 | 0 | 4 |
| DOG 6, SESSION 2 | 1 | 12 |
| DOG 6, SESSION 3 | 0 | 3 |
| DOG 7, SESSION 1 | 0 | 6 |
| DOG 7, SESSION 2 | 0 | 2 |
| DOG 7, SESSION 3 | 1 | 5 |
| DOG 8, SESSION 1 | 2 | 10 |
| DOG 8, SESSION 2 | 2 | 8 |
| DOG 8, SESSION 3 | 0 | 4 |
| DOG 9, SESSION 1 | 0 | 2 |
| DOG 9, SESSION 2 | 0 | 2 |

GASTROINTESTINAL ELECTRICAL STIMULATOR HAVING A VARIABLE ELECTRICAL STIMULUS

CROSS REFERENCE TO RELATED APPLICATION

This Application is a Continuation-In-Part of U.S. Application No. 09/254,364, now U.S. Pat. No. 6,243,607 having an International Filing Date of Sep. 4, 1997 and which entered the national phase in the United States on Jun. 7, 1999, which U.S. Application claims the benefit of U.S. Provisional Application No. 60/025,500 filed Sep. 5, 1996.

FIELD OF INVENTION

This invention relates to a device for electrical stimulation of smooth muscle comprising a portion of the gastrointestinal tract, a method for using the device of the within invention and a method for electrical stimulation of the smooth muscle.

BACKGROUND OF THE INVENTION

Many different ways of stimulating gastro-intestinal function have been explored, including pharmacological, neural, purely electrical, and combined methods. In particular, gastric electrical stimulation has been a subject of research investigation for many years:

1. Bellahsene, B. E., C. D. Lind, B. D. Schirmer, O. L. Updike, and R. W. McCallum, "Acceleration of gastric emptying with electrical stimulation in a canine model of gastroparesis" *Am. J. Physiol.* 262(5 Pt 1):G826–34, 1992;
2. Berger, T., J. Kewenter, and N. G. Kock, "Response to Gastrointestinal Pacing: Antral, Duodenal and Jejunal Motility in Control and Postoperative Patients" Annals of surgery 161:139–44, 1966;
3. Chen, J. D., B. D. Schirmer, and R. W. McCallum "Serosal and cutaneous recordings of gastric myoelectrical activity in patients with gastroparesis" *Am. J Physiol.* 266(1 Pt 1):G90–8, 1994;
4. Daniel, E. E. and S. K. Sarna "Distribution of Excitory Vagal Fibers in Canine Wall to Control Motility" *Gastroenterology* 71:608–13, 1976;
5. Familoni, B. O., T. L. Abell, G. Voeller, A. Salem, 0. Gaber, and D. Nemoto "Long-term electrical stimulation of the human stomach" *Gastroenterology* 106(2):A496, 1994;
6. Sama, S. K., K. L. Bowes, and E. E. Daniel "Gastric Pacemakers" *Gastroenterology* 70:226–31, 1976;
7. Quast, D. C., Beall, A. C., and DeBakey, M. E., "Clinical Evaluation of the Gastrointestinal Pacer" *Surg. Gynec. Obstet.* 120:35–40, 1965;
8. Miedama, B. W., Sarr, M. G., and Kelly, K. A. "Pacing the Human Stomach" *Surgery* 111:143–50, 1992;
9. Hocking M. P., Vogel, S. B., and Sininsky, C. A. "Human gastric myoelectric activity and gastric emptying following gastric surgery and with pacing" *Gastroenterology* 103:1811–1816, 1992;
10. Familoni, B. O., Abell, T. L., Nemoto D., Voeller, G., and Johnson, B. "Efficacy of electrical stimulation at frequencies higher than basal rate in canine stomach" *Digestive Diseases and Sciences* 42:892–897, 1997;
11. Christensen, J. "Responses of the smooth muscle segment of the opossum esophagus to distention and electrical stimulation, and their modification by antagonist" In: Gastrointestinal Motility, International Symposium on Motility of the Gastrointestinal tract, pp. 167–174, Erlangen, July 15–16, 1969).

It is now well known that gastric contractions are controlled by gastric electrical activity ("GEA") (Sarna et. al., 1976). Moreover, when contractions are present, their temporal and propagation organization is strongly related to the organization of GEA. Therefore, electrical stimulation of the stomach may have particular application to a condition known as gastroparesis, in which the stomach is incapable of grinding, mixing and transmitting the food to the duodenum, and to other conditions in which gastric emptying time is abnormally delayed (Bellahsene et. al., 1992; Chen et. al., 1994).

Recently, gastric electrical pacemaking has once again become a subject of intensive investigation (Eagon J C and Kelly K A "Effect of electrical stimulation on gastric electrical activity, motility and emptying" *Neurogastroenterology & Motility.* 7:39–45, 1995; The GEMS Group "Electrical stimulation for the treatment of gastroparesis—preliminary report of a multicenter international trial" *Gastroenterology*, 110:A668, 1996; Chen J D Z, Lin Z Y, Schirmer B D, Williams R D, Ross B and McCallum R W "Effect of gastric pacing with optimal parameters on gastric emptying in patients with gastroparesis" In: Proceedings of XV Int. Symposium on Gastrointestinal Motility, p. 42, Rome, Italy, October 1995; McCallum, R. W., Chen, J. D. Z., Lin, Z., Schirmer, B. D., Williams, R. D., and Ross R. A. "Gastric pacing improves emptying and symptoms in patients with gastroparesis" *Gastroenterology* 114:456–61, 1998).

In 1963, Bilgutay et. al. (Bilgutay A M, Wingrove R, Griffin W O, Bonnabeau R C and Lillehei C W "Gastrointestinal Pacing. A New Concept in the Treatment of Ileus" *Ann. Surg.*, 158;338–43, 1963) described marked shortening of the duration of postoperative ileus in patients using neural electric gastric stimulation ("NEGS") with a single antral intraluminal electrode and a single cutaneous reference electrode. However, subsequent well-controlled studies have failed to confirm any significant effect of single-electrode NEGS on antral contractions or postoperative ileus (Quast et. al., 1965 and Miedama et. al., 1992).

Later studies have focused upon Electrical Control Activity ("ECA") entrainment, termed Gastric Electrical Pacing ("GEP") by Sama et. al., 1976. Distal antral stimulation in dogs produced a delay in emptying of liquids and solids. Proximal stimulation to entrain ECA to a higher frequency was found to have no effect on antral emptying. These findings were confirmed by Kelly K A, and Code CF "Duodenal-gastric reflux and slowed gastric emptying by electrical pacing of the canine duodenal pacesetter potential" *Gastroenterol.*, 72:429, 1977. Kelly et. al., 1977 demonstrated retrograde propulsion of duodenal contents with distal duodenal stimulation and entrainment of the duodenal pacesetter potential.

J. C. Eagon et. al., 1995 studied carefully the effects of low-frequency (0–20 Hz) electrical stimulation on canine gastric electrical activity (GEA), motility and emptying and concluded that although an increment of GEA frequency was observed when stimulating at 6 and 30 cycles-per-minute (cpm), gastric contractions and emptying were not affected by stimulation in the low frequency range. More optimistic findings were reported by The GEMS Study Group, 1996 in improvement of nausea and vomiting in humans, but no dramatic change in gastric emptying was evident.

Chen et al., October 1995, described slight acceleration of gastric emptying in a pilot study of a small number of patients with gastroparesis by performing GEP at one site on the greater curvature of the stomach and entraining ECA to a frequency 10% higher than the electrophysiological or basal. Further, Bellahsene et. al., 1992, in a canine model of gastroparesis, showed acceleration of gastric emptying after glucagon-evoked dysrhythmia and GEP in five vagotomized dogs. However, the study failed to show significant improvement in gastric emptying without the artificially created dysrhythmia thus questioning the ability of GEP alone to accelerate gastric emptying.

Familoni et al., 1997 in a more recent investigation using a canine model of GEP described some increased contractile activity when stimulating with frequency 4–5 times higher than the electrophysiological, but they did not measure gastric emptying. In addition, another study (The GEMS Group, 1996) reported diminished nausea and vomiting in patients treated with GEP, but the impact of pacing on gastric emptying remained questionable.

In 1998 McCallum et al., 1998 described acceleration of gastric emptying in patients with gastroparesis by performing GEP at a single site on the greater curvature of the stomach and entraining ECA to a frequency 10% higher than the basal. However, the experimental protocol in this study provided for continuing prokinetic drug therapy during the stimulation, and therefore the effect of GEP alone remained obscured.

The within invention specifically utilizes a mathematical or computer model of gastric stimulation in order to derive the parameters of the electrical stimuli required to produce artificially propagated contractions in the stomach.

Mirrizzi et. al., 1985 (Mirrizzi N., R. Stella, U. Scafoglieri "A model of extra cellular wave shape of the gastric electrical activity" *Med. Biol. Eng. & Comput*, 23:33–37, 1985) and Mirrizzi et. al., 1986 (Mirrizzi N., R. Stella, U. Scafoglieri "Model to stimulate the gastric electrical control activity on the stomach wall and on abdominal surface" *Med. Biol. Eng. & Comput*, 24:157–163, 1986) suggest a conical dipole model of gastric electrical activity. The gastric electrical field was considered to be a result of electrical dipoles pointing towards the centre of the stomach in an approximately 2 mm. wide ring of depolarized smooth muscle cells. The conical dipole model assumes that the first such ring originates in the mid-corpus. With the continuous repolarization of the proximal layer of cells in the ring and the depolarization of the distal layer, the ring can be thought of as a dynamic entity that moves with an increasing velocity towards the pylorus, thus representing the dynamics of the depolarization-repolarization phenomena that take place in a healthy stomach.

However, a recent study by the inventors of the within invention (Mintchev, M. P. and K. L. Bowes "Conoidal Dipole Model of the Electrical Field Produced by the Human Stomach" *Med. Biol. Eng. & Comput*. 33:179–85, 1995) suggested a conoidal dipole model of gastric electric field (the "conoidal model") as an improvement over the previously known conical dipole model. In the conoidal model, as described in detail in Mintchev et. al., 1995, the area S of a δ-wide ring of depolarized cells represented as dipoles pointing toward the center was given with:

$$S = 2\pi \delta r(t) \qquad \text{Equation [1]}$$

where r(t) represented the radii of the circles that build up this ring of dipoles. On the other hand, the relationship between the vector of the dipole density D and the vector of the equivalent dipole moment P (which is directly related to the number of depolarized cells in the ring and their depolarization level) is given with:

$$D = P/S \qquad \text{Equation [2]}$$

The articles by Mirrizzi et al., 1985 and 1986, set out above, suggested that $|P|$ could be considered constant and estimated its value to be $2.2 \times 10^{-16}$ C.m. They assumed that the charge distribution on each side of a given polarized cell in the ring is approximately equal, and the number of polarized cells in the ring remains the same, while the density of the cells increases in distal direction with the decrement of S. When considering gastric stimulation in the conoidal model, this assumption is deviated from and $|P|$ is considered to be a variable. In fact, it is believed, and the conoidal model assumes, that changes in gastric electrical activity (GEA) associated with contractions cause the amplitude of this vector to fluctuate. However, these fluctuations could very well be obscured when the vector distance p between the point of interest and the infinitesimal area segment dS located on the ring of depolarized cells is sufficiently great (e.g. in electrogastrography):

$$V_Q = [1/4\pi\epsilon] \int_{(s)} [D \cdot \rho / |\rho|^3] dS \qquad \text{Equation [3]}$$

Although the conoidal model and equation [3] relate to the spontaneous GEA of a normal stomach (as is discussed further below), it is believed that the conoidal model may be able to reconstruct the temporal and propagation organization of the missing contractions in a gastroparetic stomach.

There is therefore a need for a method and a device for the electrical stimulation of smooth muscle comprising a portion of the gastro-intestinal tract in order to facilitate or aid at least a partial emptying of such portion. Further, there is a need for a method and a device for the electrical stimulation of the smooth muscle of the stomach. Finally, there is a need for a method and a device which utilize the conoidal model to derive the parameters of the electrical stimulus required to produce artificially propagated contractions in the stomach sufficient to facilitate at least a partial emptying of the stomach.

SUMMARY OF THE INVENTION

This invention relates to a device for electrical stimulation of smooth muscle comprising a portion of the gastro-intestinal tract, a method for using the device of the within invention and a method for electrical stimulation of the smooth muscle. In particular, the device and the methods relate to the electrical stimulation of the smooth muscle in a manner such that local contractions of the portion of the gastro-intestinal tract are artificially propagated therethrough in order to facilitate or aid at least a partial emptying of such portion. Preferably, the local contractions are artificially propagated by phase locking or time shifting the electrical stimulus, which is applied to the smooth muscle circumferentially about the portion at two or more locations. Further, the electrical stimulus applied at each location to produce the desired local contraction is preferably variable such that the characteristics or nature of the electrical stimulus may be varied between locations.

Preferably, when stimulating the smooth muscle of the stomach, the within invention utilizes the conoidal mathematical or computer model of gastric stimulation in order to derive the parameters of the electrical stimuli required to produce artificially propagated contractions in the stomach. Further, the conoidal model is preferably used to calculate the positions or locations for application of the electrical stimuli in the stomach, to determine the configurations of circumferential electrode sets utilized by the device of the within invention to produce the local circumferential contractions of the stomach and to determine the nature or characteristics of the phase-locked electrical stimulus applied at each location or position in order to recreate a distally moving peristalsis.

In the preferred embodiment, the within invention is directed at a method and a device for simulating gastric electrical stimulation using the conoidal model of gastric electrical activity. Thus, the invention may suggest a possible avenue toward reliable gastric pacing. Further, the invention implements the concept of artificially propagated contractions by phase-locking or time-shifting local non-propagated contractions produced by variable electrical stimuli applied at selected locations in the stomach, by circumferential electrode sets of the within invention. As described above, the temporal and propagation organization of gastric electrical activity described in the conoidal model is used to derive the geometry of the stimulating electrode sets and to determine the characteristics, nature and timing of the phase-locked electrical stimuli applied to the different circumferential electrode sets.

In a first aspect of the invention, the invention is directed at a device for electrical stimulation of smooth muscle comprising a portion of the gastro-intestinal tract, wherein the portion of the gastro-intestinal tract defines a longitudinal axis extending therethrough. The device is comprised of:

(a) a proximal electrode set for arrangement circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;

(b) at least one distal electrode set for arrangement circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;

(c) at least one power source for providing a variable electrical stimulus to the proximal and distal electrode sets sufficient to stimulate the smooth muscle to produce the local circumferential contractions, wherein the electrical stimulus is variable between each of the proximal and distal electrode sets;

(d) a timing mechanism, associated with the power source, for phase locking the electrical stimulus such that the electrical stimulus is applied to the proximal and distal electrode sets successively and repetitively;

wherein the axially spaced relationship between the electrode sets and the timing of the electrical stimulus applied to the electrode sets are selected such that the local circumferential contractions are artificially propagated distally through the portion of the gastro-intestinal tract.

In a second aspect of the invention, the invention is directed at a method for electrical stimulation of smooth muscle comprising a portion of the gastro-intestinal tract, wherein the portion of the gastro-intestinal tract defines a longitudinal axis extending therethrough and wherein the method is performed using a device comprised of a proximal electrode set and at least one distal electrode set. The method is comprised of the steps of:

(a) arranging the proximal electrode set circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;

(b) arranging each of the distal electrode sets circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;

(c) applying a variable electrical stimulus to the proximal and distal electrode sets sufficient to stimulate the smooth muscle to produce the local circumferential contractions, wherein the electrical stimulus is variable between each of the proximal and distal electrode sets and wherein the electrical stimulus is phase-locked such that the electrical stimulus is applied to the proximal and distal electrode sets successively and repetitively;

wherein the axially spaced relationship between the electrode sets and the timing of the phase-locking of the electrical stimulus applied to the electrode sets are selected such that the local circumferential contractions are artificially propagated distally through the portion of the gastro-intestinal tract.

In a third aspect of the invention, the invention is directed at a method for electrical stimulation of smooth muscle comprising a portion of the gastro-intestinal tract, wherein the portion of the gastro-intestinal tract defines a longitudinal axis extending therethrough. The method is comprised of the steps of:

(a) applying an electrical stimulus at a proximal location to the smooth muscle circumferentially about the portion of the gastro-intestinal tract in a plane substantially perpendicular to the longitudinal axis, wherein the electrical stimulus is sufficient to stimulate the smooth muscle to produce a local circumferential contraction at the proximal location;

(b) applying an electrical stimulus at at least one distal location to the smooth muscle circumferentially about the portion of the gastro-intestinal tract in a plane substantially perpendicular to the longitudinal axis, wherein the distal location is in axially spaced relationship relative to the proximal location and wherein the electrical stimulus is sufficient to stimulate the smooth muscle to produce a local circumferential contraction at the distal location and wherein the applied electrical stimulus is varied between each of the proximal and distal locations; and (c) phase-locking the electrical stimulus applied at the proximal and distal locations such that the electrical stimulus is applied at the proximal and distal locations successively and repetitively;

wherein the axially spaced relationship between the proximal and distal locations and the timing of the phase-locking of the electrical stimulus applied to the locations are selected such that the local circumferential contractions are artificially propagated distally through the portion of the gastro-intestinal tract.

In each aspect of the invention, the phase locking of the electrical stimulus is preferably comprised of the application of the variable electrical stimulus at each location or at each electrode set for an interval of time which overlaps the application of the electrical stimulus to the next successive location or electrode set. More particularly, the application of the electrical stimulus at each location or to each electrode set preferably ceases following the commencement of the application of the electrical stimulus at the next successive location or to the next successive electrode set. In other words, the application of the variable electrical stimulus at a prior location or electrode set laps over, covers, extends beyond or coincides, at least in part, with the application of the electrical stimulus to at least the next successive location or electrode set.

Preferably, the interval of time of the application of the electrical stimulus at each location or to each electrode set is selected such that each local circumferential contraction produced thereby overlaps the next successive local circumferential contraction. More particularly, each local circumferential contraction preferably ceases following the commencement of the next successive local circumferential contraction. In other words, the prior local circumferential contraction preferably laps over, covers, extends beyond or coincides, at least in part, with at least the next successive local circumferential contraction.

Thus, in the first aspect of the invention, the timing mechanism of the device preferably applies the electrical stimulus to each electrode set for an interval of time in overlapping succession such that the application of the electrical stimulus to each electrode set ceases following the commencement of the application of the electrical stimulus to the next successive electrode set. In the second aspect of the invention, the applying step of the method is preferably comprised of applying the electrical stimulus to each electrode set for an interval of time in overlapping succession such that the application of the electrical stimulus to each electrode set ceases following the commencement of the application of the electrical stimulus to the next successive electrode set. Finally, in the third aspect of the invention, the phase-locking step of the method is preferably comprised of applying the electrical stimulus at each location for an interval of time in overlapping succession such that the application of the electrical stimulus at each location ceases following the commencement of the application of the electrical stimulus at the next successive location.

In each aspect, the interval of time of application of the electrical stimulus to each electrode set or at each location is variable between successive electrode sets or successive locations respectively. For instance, in the third aspect of the invention, the interval of time of application of the electrical stimulus at each proximal and distal location is variable between successive locations. In other words, the interval of time for which the electrical stimulus is applied may vary between one or more locations or between one or more electrode sets. Thus, as a result, the period or length of each local circumferential contraction produced thereby may also vary.

However, although the interval of time may vary as described, the interval of time of application of the electrical stimulus preferably decreases with each successive electrical stimulus. Thus, the interval of time of application of the electrical stimulus to each electrode set preferably decreases with each successive electrode set. Similarly, the interval of time of application of the electrical stimulus at each location preferably decreases with each successive location. Accordingly, the period or length of each local circumferential contraction produced thereby may also decrease with each successive local circumferential contraction.

As indicated, the interval of time of the application of each electrical stimulus is selected such that the application of each electrical stimulus ceases following the commencement of the application of the next successive electrical stimulus. However, preferably, the application of each electrical stimulus ceases following the commencement of the application of all successive electrical stimulus.

Further, the interval of time of the application of each electrical stimulus may be selected such that each local circumferential contraction produced thereby ceases following the commencement of the next successive local circumferential contraction. In addition, the interval of time of the application of each electrical stimulus may be selected such that each local circumferential contraction produced thereby ceases following the commencement of all successive local circumferential contractions.

In the preferred embodiment of the first aspect of the invention, the timing mechanism of the device applies the electrical stimulus to each electrode set for an interval of time in overlapping succession such that the application of the electrical stimulus to each electrode set ceases following the commencement of the application of the electrical stimulus to all successive electrode sets.

In the preferred embodiment of the second aspect of the invention, the applying step of the method is comprised of applying the electrical stimulus to each electrode set for an interval of time in overlapping succession such that the application of the electrical stimulus to each electrode set ceases following the commencement of the application of the electrical stimulus to all successive electrode sets.

Finally, in the preferred embodiment of the third aspect of the invention, the phase-locking step of the method is comprised of applying the electrical stimulus at each location for an interval of time in overlapping succession such that the application of the electrical stimulus at each location ceases following the commencement of the application of the electrical stimulus at all successive locations.

Further, the application of the electrical stimulus to each electrode set or at each location may cease at any time following the commencement of the application of the electrical stimulus at all successive electrode sets or locations respectively. However, preferably, the application of the electrical stimulus to each electrode set or at each location ceases substantially concurrently. Thus, the application of the electrical stimulus to each proximal and distal electrode sets preferably ceases substantially concurrently or at about the same time. Similarly, the application of the electrical stimulus at each proximal and distal location preferably ceases substantially concurrently or at about the same time.

Each electrical stimulus may be applied at each location or to each electrode set for any interval of time sufficient to produce the desired local circumferential contraction. However, preferably, the interval of time of the application of the electrical stimulus to each proximal and distal electrode set is less than or equal to about 24 seconds. Similarly, the applying step of the method is comprised of applying the electrical stimulus to each successive electrode set for an interval of time of less than or equal to about 24 seconds. Finally, the phase-locking step of the method is comprised of applying the electrical stimulus at each successive location for an interval of time of less than or equal to about 24 seconds. In the preferred embodiment of the invention in any aspect, the interval of time of application of the electrical stimulus is between about 4 to 24 seconds.

Preferably, in all aspects of the invention, a period of stimulation is provided in which an electrical stimulus is successively applied at each location or to each electrode set, followed by a period of no stimulation, or a period of rest, before repeating the application of the electrical stimuli.

During the period of stimulation, the desired local circumferential contractions are artificially propagated distally through the portion of the gastro-intestinal tract. The period of no stimulation is provided prior to repeating the period of stimulation and the repetition of the artificial propagation of the local circumferential contractions.

Thus, in the first aspect of the invention, the timing mechanism of the device applies the electrical stimulus to the proximal and distal electrode sets such that the electrical stimulus is applied to the proximal and distal electrode sets in succession for a period of stimulation, following which there is a period of no stimulation before the next application of the electrical stimulus to the proximal and distal electrode sets. In the second aspect of the invention, the applying step of the method performed using the device is comprised of applying the electrical stimulus to the proximal and distal electrode sets such that the electrical stimulus is applied to the proximal and distal electrode sets in succession for a period of stimulation, following which there is a period of no stimulation before the next application of the electrical stimulus to the proximal and distal electrode sets. Finally, in the third aspect of the invention, the phase-locking step of the method is comprised of applying the electrical stimulus at the proximal and distal locations such that the electrical stimulus is applied at the proximal and distal locations in succession for a period of stimulation, following which there is a period of no stimulation before the next application of the electrical stimulus at the proximal and distal locations.

In all aspects of the invention, the period of no stimulation may be of any period or length of time and may be of any period or length of time relative to the period of stimulation. Preferably, the period of no stimulation is substantially equal to the period of stimulation. Further, the period of stimulation and the equivalent period of no stimulation are both selected to provide a period or length of time sufficient to permit the electrical stimulus to produce the local circumferential contractions and to permit the artificial propagation of the contractions through the portion of the gastro-intestinal tract, preferably in a manner facilitating at least a partial emptying thereof.

In the first, second and third aspects of the invention, the portion of the gastro-intestinal tract may be comprised of the esophagus, the stomach, the small intestine, the large intestine, the anal sphincter and combinations thereof. However, in the preferred embodiment, the portion of the gastro-intestinal tract is comprised of the stomach. Further, in all aspects of the invention, the artificial propagation of local contractions through the gastro-intestinal tract, and in particular the stomach, is preferably sufficient to facilitate at least a partial emptying thereof.

The electrical stimulus may be applied at any location which permits the electrical stimulus to produce a local contraction at the desired portion of the gastro-intestinal tract. Thus, the electrode sets of the device may be affixed, applied or implanted at any such location. However, preferably, the electrical stimulus is applied at a location in communication with, or within, the layers comprising the wall of the gastro-intestinal tract. In the preferred embodiment, the electrical stimulus is applied subserosally. Thus, the electrode sets of the device are preferably implanted subserosally in the gastro-intestinal tract.

Further, in the third aspect of the invention, the electrical stimulus is preferably applied at at least two distal locations, and more preferably, at at least three distal locations. The number of distal locations will be determined by, amongst other factors, the size or dimensions, and in particular the length, of the portion of the gastro-intestinal tract to be stimulated and by the desired parameters and effectiveness of the artificially propagated local circumferential contractions. In the preferred embodiment, the electrical stimulus is applied at three to five distal locations.

Similarly, in the first and second aspects of the invention, the device is preferably comprised of at least two distal electrode sets, and more preferably, at least three distal electrode sets. The number of distal electrode sets will similarly be determined by, amongst other factors, the size or dimensions, and in particular the length, of the portion of the gastro-intestinal tract to be stimulated and by the desired parameters and effectiveness of the artificially propagated local circumferential contractions. In the preferred embodiment, the device is comprised of three to five distal electrode sets. Thus, the device preferably includes a total of four to six electrode sets.

In the preferred embodiment, the proximal location is located in about the mid-corpus of the stomach. The distal locations are located distally to the proximal location and in an axially spaced relationship with each other such that the phase-locking of the electrical stimulus produces a local circumferential contraction at the proximal location and each distal location in succession. Similarly, the proximal electrode set is located in about the mid-corpus of the stomach. The distal electrode sets are located distally to the proximal electrode set and in an axially spaced relationship with each other such that the phase-locked electrical stimulus produces a local circumferential contraction at the proximal electrode set and each distal electrode set in succession.

As well, in the first and second aspects of the invention, each of the proximal and distal electrode sets of the device is comprised of at least one active electrode and at least one ground electrode. Preferably, the active electrodes are connected to the power source, and the electrical stimulus is applied to the active electrodes, in a manner such that the electrical stimulus is provided concurrently to each of the active electrodes included in an electrode set.

In the preferred embodiment, each active electrode is paired with a ground electrode. However, the active electrodes may share one or more ground electrodes. For example, the electrode set may be comprised of a single ground electrode and one or more active electrodes. Thus, in the preferred embodiment, the number of active electrodes is greater than or equal to the number of ground electrodes in each of the proximal and distal electrode sets.

The electrodes of each electrode set may be spaced apart circumferentially about the portion of the gastro-intestinal tract at any distance permitting the electrical stimulus to produce a local circumferential contraction. However, in the preferred embodiment, the distance between the electrodes in each of the proximal and distal electrode sets is between about 2 to 4 centimeters. Thus, the specific number of electrodes comprising an electrode set will be dependent upon the specific circumference of the portion of the gastro-intestinal tract at the location of the electrode set.

Although the electrical stimulus applied at each of the proximal and distal locations, and to the proximal and distal electrodes, may be either direct or alternating, the electrical stimulus is preferably alternating. Thus, in the first aspect of the invention regarding the device, the electrical stimulus is preferably provided by an alternating voltage source. Further, although the electrical stimulus is variable and may be varied between each of the locations or electrode sets, all of the electrical stimuli are preferably alternating.

As well, although the alternating electrical stimulus may be either monopolar or bipolar, the alternating electrical stimulus is preferably bipolar. Thus, the alternating voltage source of the device is preferably a bipolar alternating voltage source. Again, although the electrical stimulus is variable and may be varied between each of the locations or electrode sets, all of the electrical stimuli are preferably bipolar.

Finally, each alternating electrical stimulus may have any shape suitable for producing the local circumferential contractions. However, the shape of each alternating electrical stimulus is preferably rectangular or square. Thus, the alternating voltage source is preferably a rectangular alternating voltage source or a square alternating voltage source. Further, although the shape of the alternating electrical stimulus is variable and may be varied between each of the locations or electrode sets, all of the alternating electrical stimuli are preferably rectangular or square.

Each alternating voltage source and each alternating electrical stimulus may have any frequency compatible with and capable of producing the desired local circumferential contraction without causing any significant damage to the tissues of the gastro-intestinal tract. However, the frequency of each alternating voltage source, in the first aspect of the invention, and the frequency of each alternating electrical stimulus, in the second and third aspects of the invention, is preferably between about 5 to 500 Hertz, and more preferably, is between about 5 to 50 Hertz, wherein the frequency is variable between each of the locations or electrode sets. In the preferred embodiment, the frequency is about 50 Hertz. Further, although the frequency of the alternating electrical stimulus or the alternating voltage source is variable and may be varied between each of the locations or electrode sets, the frequency of every alternating electrical stimuli or every alternating voltage source is preferably substantially the same, being about 50 Hertz in the preferred embodiment.

Each alternating voltage source and each alternating electrical stimulus may have any voltage compatible with and capable of producing the desired local circumferential contraction without causing any significant damage to the tissues of the gastrointestinal tract. However, the voltage of the alternating voltage source, in the first aspect of the invention, and the voltage of the alternating electrical stimulus, in the second and third aspects of the invention, is preferably less than or equal to about 20 Volts, peak to peak, and more preferably, is less than or equal to about 15 Volts, peak to peak, wherein the voltage is variable between each of the locations or electrode sets. In the preferred embodiment, the voltage is between about 4 to 14 Volts, peak to peak.

Further, as stated, the voltage of the alternating electrical stimulus or the alternating voltage source is variable and may be varied between each of the locations or electrode sets. Preferably, the voltage of the alternating electrical stimulus or the alternating voltage source decreases with each successive location or electrode set. Thus, in the second aspect of the invention, the applying step of the method is preferably comprised of varying the voltage of the alternating electrical stimulus between each of the proximal and distal electrode sets. More preferably, the applying step of the method is comprised of decreasing the voltage of the alternating electrical stimulus applied to each successive electrode set. In the third aspect of the invention, the voltage of the alternating electrical stimulus applied at the proximal location preferably varies from the voltage of the alternating electrical stimulus applied at each successive distal location. More preferably, a decreasing voltage is applied at each successive location.

BRIEF DESCRIPTION OF DRAWINGS

Embodiments of the invention will be described with reference to the accompanying tables and drawings, in which:

FIG. 1 shows a simulated pacing session produced by a model of the within invention in a first study conducted by the inventors;

FIG. 8 is a table showing the effect of the application of the electrical stimuli, as shown in FIGS. 6 and 7 for the third study, on the gastric emptying of 200 ml of water;

FIG. 15 shows a preferred embodiment of the phase-locking of the electrical stimuli as applied to six sets of circumferentially implanted electrodes;

FIG. 16 is a table showing the effect of the application of the electrical stimuli on the gastric emptying of food pellets for the fourth study conducted by the inventors.

DETAILED DESCRIPTION OF THE INVENTION

Figure 2:
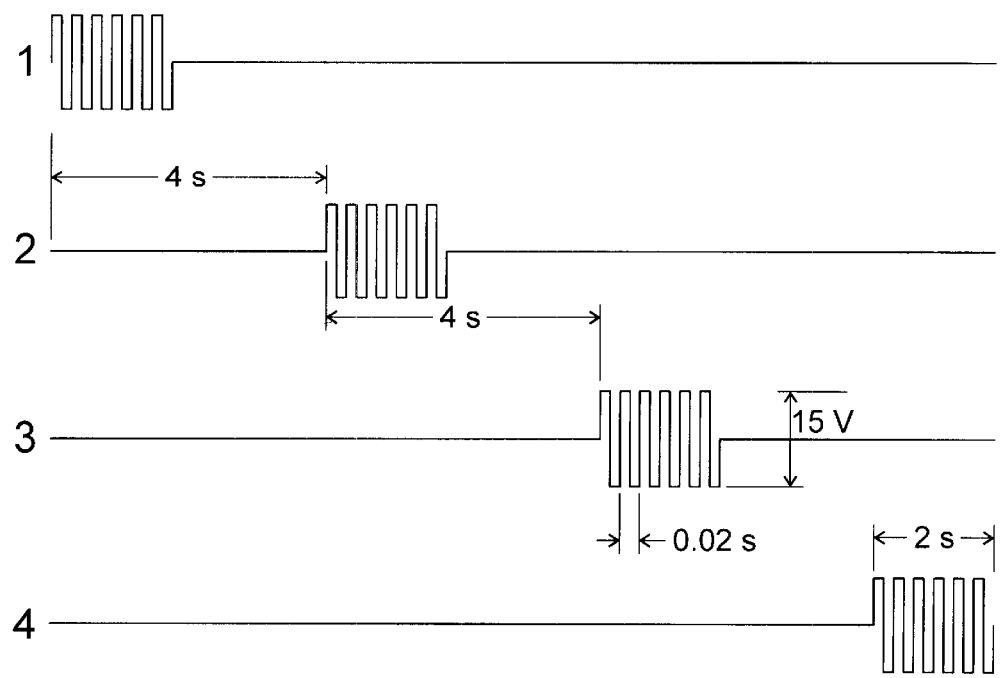
FIG. 2 shows the phase-locking of the electrical stimuli which produced the contractions shown in FIG. 1.

This invention relates to a device (20) for electrical stimulation of smooth muscle comprising a portion of the gastro-intestinal tract, a method for using the device (20) of the within invention and a method for electrical stimulation of the smooth muscle. In the preferred embodiment, the device (20) and the methods relate to the electrical stimulation of the smooth muscle in a manner such that local contractions of the portion of the gastro-intestinal tract are artificially propagated distally therethrough in order to facilitate or aid at least a partial emptying of such portion.

The local contractions are artificially propagated by phase locking or time shifting a variable electrical stimulus, which is applied to the smooth muscle circumferentially about the portion at two or more locations.

The portion of the gastro-intestinal tract may be comprised of the esophagus, the stomach, the small intestine, the large intestine, the anal sphincter and combinations thereof. However, in the preferred embodiment, the portion of the gastro-intestinal tract is comprised of the stomach. Further, the portion of the gastrointestinal tract defines a longitudinal axis extending therethrough. In the stomach, the longitudinal axis is centrally or equidistantly located between the greater and lesser curvatures of the stomach.

The variable electrical stimulus may be applied at any location in the body of the patient, being an animal including a human, or the gastrointestinal system of the patient which permits the electrical stimulus to produce a local contraction at the desired portion of the gastro-intestinal tract. However, preferably, the electrical stimulus is applied at a location in communication with, or within, the layers comprising the wall of the gastro-intestinal tract. In the preferred embodiment, the electrical stimulus is applied subserosally.

The invention provides electrical stimulation to the smooth muscle of the selected portion of the gastro-intestinal tract, which smooth muscle is preferably comprised of innervated muscle tissue. Although the muscle tissue itself may be directly stimulated, in the preferred embodiment, as discussed further below, it is theorized that the smooth muscle is neurally electrically stimulated through the nerves associated with and innervating the muscle tissue in order to produce the contraction of the smooth muscle. Thus, in the preferred embodiment, the invention is used in patients with intact local gastric nerves. The invention may not be useful in patients with impaired local cholinergic nerves.

Further, as stated above, when stimulating the smooth muscle of the stomach, the within invention attempts to create a simulated system that reproduces the spatial and temporal organization of normal gastric electrical activity by creating and controlling local circumferential non-propagated contractions. In this simulated gastric pacing system, each local circumferential contraction is invoked by applying an electrical stimulus to the smooth muscle circumferentially about the portion of the gastro-intestinal tract in a plane substantially perpendicular to the longitudinal axis of the portion. The electrical stimulus is applied at a proximal location and at at least one distal location. The distal location is in axially spaced relationship relative to the proximal location. Further, the applied electrical stimulus is selected to be sufficient to stimulate the smooth muscle to produce the local circumferential contractions at the proximal and distal locations.

In the device (20) of the within invention, the device (20) is comprised of a proximal electrode set (24) and at least one distal electrode set (26). The proximal electrode set is arranged circumferentially at the proximal location, while the distal electrode set (26) is arranged at the distal location. The proximal and distal electrode sets (24, 26) are arranged circumferentially in the plane substantially perpendicular to the longitudinal axis of the portion of the gastro-intestinal tract. Further, the electrode sets (24, 26) are provided with an electrical stimulus sufficient to stimulate the smooth muscle to produce the local circumferential contractions at the locations of the electrode sets (24, 26) by at least one power source (22).

Further, the electrical stimulus stimulating the smooth muscle is phase-locked such that the electrical stimulus is applied at the proximal and distal locations successively and repetitively. In the device (20), the device (20) is further comprised of a timing mechanism (28) associated with the power source (22) for phase locking the electrical stimulus such that the electrical stimulus is applied to the proximal and distal electrode sets (24, 26) successively and repetitively. The axially spaced relationship between the proximal and distal locations, or the proximal and distal electrode sets (24, 26) of the device (20), and the timing of the phase-locking of the variable electrical stimulus are selected such that the local circumferential contractions are artificially propagated distally through the portion of the gastro-intestinal tract. In the preferred embodiment, the conoidal mathematical or computer model of gastric stimulation is used to derive the specific parameters of the electrical stimuli required to produce the artificially propagated contractions.

Spontaneous mechanical activity of the portion of the gastro-intestinal tract, such as the stomach in the preferred embodiment, could interfere negatively with the artificially invoked and propagated local contractions. Therefore, in the preferred embodiment, the within invention is used in circumstances of gastroparesis or abnormally delayed gastric emptying.

As stated, the within invention is based upon the conoidal dipole model of gastric electrical activity, as described earlier, and implies that artificially propagated gastric contractions can be produced by circumferential stimulation of the smooth muscle, using circumferential sets of stimulating electrodes (24, 26), and by phase-locking the applied electrical stimulus. The suggested conoidal model is used to derive the geometry of the stimulating electrode sets, the electrode set positions and the actual phase-locking or timing of the application of the stimulating electrical stimulus. Of course, the model has the limitations of any mathematical approximation of a real-life physiological phenomenon. However, it is believed that most of the assumptions made in this model are relevant to the electrophysiology of the human stomach. This is supported by the test data set out below.

However, producing artificially propagated contractions does not necessarily mean that an adequate gastric emptying would be obtained, nor does it mean that the set of stimulating electrodes used in this model should not be modified as real-life experiments on animals and humans indicate. Preferably, however, the artificial propagation of the local contractions through the portion of the gastro-intestinal tract, such as the stomach, is sufficient to facilitate at least a partial emptying thereof. Thus, the artificially contracting stomach may need to be synchronized with any spontaneous contractions of the duodenum or opening of the pylorus. The potential requirement for synchronization may be addressed by utilizing biofeedback from the duodenum to control gastric electrical stimulation. Further, if the proximal duodenum or pylorus are mechanically inactive, the implantation of electrodes on the pylorus or duodenum may be required, which are stimulated in synchronization with the electrodes in the stomach. However, it is possible that the duodenum may regulate itself based upon the artificial gastric contractions.

With respect to the mathematical model, as stated, the conoidal dipole model and equation [3] relate to the spontaneous gastric electrical activity of a normal stomach. Therefore, it is theorized that the following possible problems may arise which are related to the eventual abnormalities associated with the occurrence and propagation of the depolarization ring. Note that these abnormalities tend to be strongly related to abnormal gastric function:

(a) The ring of depolarized cells in a dysfunctional stomach may not have the same characteristics as the ring of depolarized cells observed in healthy subjects;

(b) The propagation of the ring in a distal direction may be disturbed; and (c) More than one depolarization ring may exist at the same time on the stomach wall.

Potential problem (a) simply indicates that the vector P in the conoidal dipole model of a dysfunctional stomach may not have the same value and possibly the same direction as the P-vector associated with normal stomachs. The second potential problem (b) implies that the mathematical expression describing the propagation of the ring in the conoidal model may not be completely accurate and may require substitution with a refined model which defines the new pathological behavior of the stomach, as such pathologies become known and understood. The third potential problem (c) is related to the phenomenon of gastric electrical uncoupling and indicates that the stomach can be split into several different areas. In each of these areas there may be a separate ring of depolarized cells that has its own vector P and law of propagation.

Stimulation might be required when each of the above problems exists separately or any combination of these problems is present. However, it is difficult, if not impossible, to separate quantitatively the problems and determine their relative significance in a given pathological situation. However, it may be assumed that in most cases, a stomach that would need pacing would be gastroparetic, i.e., its spontaneous mechanical activity would be minimal, or non-existent. Therefore, in the preferred embodiment, the within invention is used in circumstances of gastroparesis or abnormally delayed gastric emptying.

As stated, it is well known that gastric contractions are controlled by GEA. Moreover, the temporal and propagation organization of these contractions is strongly related to the organization of GEA. Therefore, according to the within invention, the temporal and propagation organization of the missing contractions are attempted to be reconstructed in a gastroparetic stomach using the existing conoidal model of gastric electric field, thus deriving a computer model of gastric electrical stimulation. The conoidal model may be used to calculate the positions and determine the configurations of the circumferential electrode sets needed to produce the local circumferential contractions and to determine the delays between the phase-locked stimuli or the timing of the stimuli, including the period or interval of stimulation and the period or interval of no stimulation, applied to these electrode sets so that a distally moving peristalsis is recreated.

Ideally, in order to facilitate a partial or complete emptying of a gastroparetic stomach, it is preferable to recreate the temporal and propagation organization of gastric contractions common for the average healthy animal or human. The within invention does this by invoking local circumferential contractions and artificially propagating them distally towards the pylorus. The primary issues which are preferably addressed to accomplish this purpose are: (1) the geometry of the stimulating electrodes that may be used to produce the local circumferential contraction; (2) the nature or characteristics of the variable electrical stimulus, including its frequency and duration, that may produce such contraction; and (3) the manner in which the applied electrical stimulus may be phase-locked or timed so that local circumferential contractions may be propagated from one electrode set to the next.

In order to address and determine the above three points, the following assumptions have been made with respect to the conoidal model of the within invention:

(a) regardless of whether the simulated stomach (a truncated conoid in a spherical system of coordinates) is able to produce an adequate ring of depolarized cells or not, and regardless of whether and how this ring moves distally, there are preferably no contractions taking place in the stomach, i.e. there is preferably a complete gastroparesis and the organization and propagation of gastric contractions need to be recreated;

(b) the local contraction produced between the active and the ground electrode of a given electrode pair would displace the stomach wall towards the longitudinal axis of the stomach by approximately 1–3 cm (depending on the amplitude of the stimulus) and would not propagate distally;

(c) phasic contractions take place simultaneously in circumferential planes (Mintchev et. al., 1995; Mirrizzi et. al., 1985; and Mirrizzi et. al., 1986. );

(d) phasic contractions propagate with an increasing velocity towards the pylorus and have well-known temporal organization (Mintchev et. al. 1995; Mirrizzi et. al. 1985; and Mirrizzi et. al. 1986)

(e) only one circumferential contraction is present in the stomach at any given moment;

(f) only antral contractions are important from a mechanical point of view.

Further, in the conoidal computer model of the within invention, it is assumed that the velocity of propagation (in cm/s) of the depolarization wave along the longitudinal axis of the stomach of an average human can be expressed with:

$$v(t)=0.00825-0.00575[(\exp(-0.362t)], \qquad \text{Equation [4]}$$

where t=0, 1, 2 . . . 19 represents the discrete time (in seconds) for which the depolarized ring propagates from its origin in the mid corpus to the pylorus. The model considers the differences in the velocities of propagation along the greater and lesser curvatures as well. In order to incorporate these concepts into the stimulation modeling, the following additional assumptions have been made:

(a) the propagation of the band of depolarization takes place from the mid corpus (second No.0) towards the pylorus (second No.19) with an increasing and known velocity;

(b) the time is discrete from 0 (the origin of the depolarization wave in the mid corpus) to 19 (distal pylorus) seconds, with a step of 1 second;

(c) the first proximal set of stimulating electrodes (24) is placed in the proximal antrum at a position reached by the propagating depolarization band (described in the original conoidal model) at second No.7;

(d) each subsequent distal set of stimulating electrodes (26) is located at a position corresponding to about a 4 to 8-second shift with respect to the previous electrode set (24, 26).

The exact distance of the circumferential electrode sets (24, 26) from the initial position of the depolarization ring in the mid corpus can be estimated from the exponential equation [4] for the velocity of propagation in an average human stomach:

$$1 = \sum \{[v(t) + v(t+1)]/2\} \cdot T; t = 0, 1, 2 \ldots T_e - 1, \qquad \text{Equation [5]}$$

where $T_e$ is the second associated with the given electrode position and T=1 s.

The circumference of a given circle on which an electrode set (24, 26) is positioned is determined by the radius of that circle. This radius, which could be regarded as a function of the discrete time, is calculated using previously described technique (Mintchev et.al., 1995). The number of electrodes in a given set (24, 26) may be calculated easily knowing the circumference and assuming that the interelectrode distance is between about 2 and 4 cm in the preferred embodiment of the invention.

In the preferred embodiment, each of the proximal and distal electrode sets (24, 26) of the device (20) is comprised of at least one active electrode (30) and at least one ground electrode (32). Preferably, the active electrodes (30) are connected to the power source, and the electrical stimulus is applied to the active electrodes (30), in a manner such that the electrical stimulus is provided concurrently to each of the active electrodes (30) included in an electrode set (24, 26).

Further, in the preferred embodiment, each active electrode (30) is paired with a ground electrode (32) to define an electrode pair. However, the active electrodes (30) may share one or more ground electrodes (32). For example, the electrode set (24, 26) may be comprised of a single ground electrode (32) and one or more active electrodes (30). Thus, in the preferred embodiment, the number of active electrodes (30) is greater than or equal to the number of ground electrodes (32) in each of the proximal and distal electrode sets (24, 26). The number of electrode pairs will therefore be determined by the number of active (30) electrodes.

The electrodes (30, 32) of each electrode set (24, 26) may be spaced apart circumferentially about the stomach or other portion of the gastro-intestinal tract at any distance permitting the electrical stimulus to produce a local circumferential contraction. However, as stated, in the preferred embodiment, the distance between the electrodes (30, 32) in each of the proximal and distal electrode sets (24, 26) is between about 2 to 4 centimeters. Thus, as stated, the specific number of electrodes (30, 32) comprising an electrode set (24, 26) will be dependent upon the specific circumference of the portion of the gastro-intestinal tract at the location of the electrode set (24, 26)

Using these principles and the conoidal model, a net of circumferential stimulating electrodes is built up on the truncated conoid representing the stomach. All active electrodes (30) and all ground or reference electrodes (32) in a given circumferential setup are separately "short-circuited", i.e. the active electrodes (30) simultaneously delivered one and the same electrical stimulus, while the ground electrodes (32) are attached to one and the same ground.

The electrical stimulus is preferably applied at at least two distal locations, and more preferably, at at least three distal locations. In the preferred embodiment, the electrical stimulus is applied at three to five distal locations. Thus, the total number of proximal and distal locations is preferably between four to six locations. However, the number of distal locations will be determined by, amongst other factors, the size or dimensions, and in particular the length, of the portion of the gastro-intestinal tract to be stimulated and by the desired parameters and effectiveness of the artificially propagated local circumferential contractions. Similarly, the device (20) is also preferably comprised of at least two distal electrode sets (26), and more preferably, at least three distal electrode sets (26). In the preferred embodiment, the device (20) is comprised of three to five distal electrode sets (26). Thus, the total number of both proximal and distal electrode sets (24, 26) is preferably between four to six electrode sets.

As indicated, in the preferred embodiment, the proximal location, and thus the location of the proximal electrode set (24), is in about the mid-corpus of the stomach. The distal locations, and thus the locations of the distal electrode sets (26), are distal to the proximal location, or proximal electrode set (24), and in an axially spaced relationship with each other such that the phase-locking of the electrical stimulus produces a local circumferential contraction at the locations in succession.

Using the conoidal model for the application of these principles to an average normal stomach, the proximal and three distal electrode sets (24, 26) preferably have 6, 5, 4 and 3 electrodes respectively. The proximal electrode set (24) comprising 6 electrodes is positioned 5.1 cm distally from the mid-corpus. Table 1 shows the distances between the circumferential electrode sets (24,26) calculated from the central line between the greater and the lesser curvatures or along the longitudinal axis of the stomach. These distances were calculated using equations [4] and [5]. In an actual setup, the arrangement of the electrode sets (24, 26) preferably starts from the most distal set (Electrode Set No.4, the closest to the pylorus), since the area of the mid-corpus is not very clearly defined anatomically.

TABLE 1

Distances between different circumferential electrode sets estimated on the central line between the greater and the lesser curvatures on the anterior gastric wall, based upon the conoidal model

|  | Mid-Corpus - Electrode Set 1 | Electrode Set 1– Electrode Set 2 | Electrode Set 2– Electrode Set 3 | Electrode Set 3– Electrode Set 4 |
|---|---|---|---|---|
| Distances cm | 5.1 | 3.23 | 3.29 | 3.36 |

The circumference of the proximal location, or the most proximal circle of the gastric conoid on which the proximal electrode set (24) was placed, was found to be 19.48 cm. Accordingly, the six stimulating electrodes were positioned 3.24 cm apart. Table 2 shows the number of stimulating electrodes (30) and the interelectrode distances in each of the four stimulating electrode sets (24, 26).

TABLE 2

Number of electrodes in a given circumferential electrode set and the distances between the individual electrodes in the set, based upon the conoidal model

|  | Electrode Set 1 (most proximal) | Electrode Set 2 | Electrode Set 3 | Electrode Set 4 |
|---|---|---|---|---|
| Number of Electrodes | 6 | 5 | 4 | 3 |
| Interelectrode Distance (cm) | 3.24 | 3.45 | 3.41 | 2.93 |

FIG. 1 shows a simulated pacing session produced by the model. The phase-locking of the electrical stimuli that produced the simulated contractions is shown on FIG. 2. However, more preferably, the electrical stimulus is variable between electrode sets. In addition, in the preferred embodiment, the phase-locking or pacing of the electrical stimuli is in accordance with that shown in FIGS. 14 and 15 for six and four electrode sets (24, 26) respectively.

The electrical stimulus applied at each of the proximal and distal locations, and to each of the proximal and distal electrodes (24, 26), may be either direct or alternating. However, the electrical stimulus is preferably alternating. Thus, in the device (20), the electrical stimulus is preferably provided by an alternating voltage source. Further, although the electrical stimulus is variable and may be varied between each of the locations or electrode sets, all of the electrical stimuli are preferably alternating.

Further, the alternating electrical stimulus may be either monopolar or bipolar. However, the alternating electrical stimulus is preferably bipolar. Thus, the alternating voltage source of the device (20) is preferably a bipolar alternating voltage source. Again, although the electrical stimulus is variable and may be varied between each of the locations or electrode sets (24, 26), all of the electrical stimuli are preferably bipolar.

As well, each alternating electrical stimulus may have any shape suitable for producing the local circumferential contractions, such as square, rectangular, sinusoidal or sawtooth. However, the shape of the alternating electrical stimulus is preferably rectangular or square. Thus, the alternating voltage source of the device (20) is preferably a rectangular alternating voltage source or a square alternating voltage source. Further, although the shape of the alternating electrical stimulus is variable and may be varied between each of the locations or electrode sets (24, 26), all of the alternating electrical stimuli are preferably rectangular or square.

The frequency of each alternating voltage source and the frequency of each alternating electrical stimulus is preferably between about 5 to 500 Hertz, and more preferably, is between about 5 to 50 Hertz, wherein the frequency is variable or may be varied as desired between each of the locations or electrode sets (24, 26). In the preferred embodiment, the frequency is about 50 Hertz. Further, although the frequency of the alternating electrical stimulus or the alternating voltage source is variable and may be varied between each of the locations or electrode sets (24, 26), the frequency of every alternating electrical stimuli or every alternating voltage source is preferably substantially the same, being about 50 Hertz in the preferred embodiment.

The voltage of the alternating voltage source and the voltage of the alternating electrical stimulus is preferably less than or equal to about 20 Volts, peak to peak, and more preferably, is less than or equal to about 15 Volts, peak to peak, wherein the voltage is variable or may be varied between each of the locations or electrode sets (24, 26). In the preferred embodiment, the voltage is between about 4 to 14 Volts, peak to peak.

Further, as stated, the voltage of the alternating electrical stimulus or the alternating voltage source is variable and may be varied between each of the locations or electrode sets (24, 26). Preferably, the voltage of the alternating electrical stimulus or the alternating voltage source is in fact varied between each successive location or electrode set (26), and more preferably, the voltage decreases with each successive location or electrode set (26).

However, the voltage and frequency of the alternating voltage source, or the alternating electrical stimulus, may be any voltage and frequency sufficient to produce the local circumferential contractions without causing any significant damage to the tissues of the gastro-intestinal tract.

For instance, the studies discussed below suggest that higher and lower voltages and higher and lower frequencies may be used as long as local circumferential contractions are produced and as long as the surrounding stomach tissue is not damaged by the electrical stimuli. In order to avoid damage, it has been found that as the voltage applied to the electrode sets (24, 26) increases, the frequency of the alternating electrical stimulus should also increase. Specifically, the frequency and voltage of the electrical stimulus are chosen in order to obtain relatively strong local contractions without causing any damage to the surrounding tissues.

Finally, the variable electrical stimulus is phase-locked or time-shifted in order to artificially propagate the contractions distally through the stomach. Phase-locking or time shifting refers to the control of the timing of the applied electrical stimuli in order to result in an artificially propagated "wave" through the stomach. The axially spaced relationship between the proximal and distal locations, or the proximal and distal electrode sets (24, 26), and the timing of the applied electrical stimulus are selected such that the local circumferential contractions are artificially propagated distally through the stomach.

Further, the variable electrical stimulus is phase-locked or timed such that the electrical stimulus is applied at each location or to each electrode set (24, 26) for an interval of time which overlaps the interval of time of the application of the electrical stimulus to the next successive location or electrode set (24, 26). In other words, the electrical stimulus is applied at each location or to each electrode set (24, 26) for an interval of time which laps over, covers, extends beyond or coincides, at least in part, with the application of the electrical stimulus to at least the next successive location or electrode set (24, 26). Thus, the application of the electrical stimulus at the proximal location or to the proximal electrode set (24) ceases following the commencement of the application of the electrical stimulus at the first distal location or to the first distal electrode set (26). Similarly, the application of the electrical stimulus at the first distal location or to the first distal electrode set (26) ceases following the commencement of the application of the electrical stimulus at the next successive distal location or to the next successive distal electrode set (26), and so on.

More particularly, in the preferred embodiment, the application of each electrical stimulus ceases following the commencement of the application of all successive electrical stimuli. Further, although the application of the electrical stimulus to each electrode set (24, 26) or at each location may cease at any time following the commencement of the application of the electrical stimulus to all successive electrode sets (26) or at all successive locations respectively, the application of the electrical stimulus to each electrode set (24, 26) or at each location ceases substantially concurrently or at about the same time in the preferred embodiment. In other words, the commencement of the application of each electrical stimulus is staggered or occurs in succession while the cessation of the application of each electrical stimulus occurs substantially concurrently or simultaneously.

As a result, in the preferred embodiment, the particular period or interval of time of application of the electrical stimulus to each electrode set (24, 26) or at each location varies between electrode sets (24, 26) or locations respectively. More particularly, the interval of time of application of the electrical stimulus decreases with each successive electrical stimulus.

The particular or specific length of the interval of time of application of each electrical stimulus is selected to produce the desired local circumferential contraction. In this regard, it has been found that desirable results occur when the interval of time of the application of the electrical stimulus to each proximal and distal electrode set (24, 26) or at each proximal and distal location is less than or equal to about 24 seconds. More preferably, the interval of time of application of each electrical stimulus is between about 4 to 24 seconds, wherein the interval of time of application of the electrical stimulus decreases with each successive electrical stimulus.

As stated, the length of the interval of time of application of each electrical stimulus is selected to produce the desired local circumferential contraction. Further, preferably, the interval of time of the application of the electrical stimulus is selected and the electrical stimuli are phase-locked such that each local circumferential contraction produced thereby overlaps the next successive local circumferential contraction. Thus, each local circumferential contraction ceases following the commencement of the next successive local circumferential contraction, and preferably, ceases following the commencement of all successive local circumferential contractions.

In addition, in the preferred embodiment, a period of stimulation is provided in which an electrical stimulus is successively applied at each location or to each electrode set (24, 26), followed by a period of no stimulation, or a period of rest, before repeating the application of the electrical stimuli. During the period of stimulation, the desired local circumferential contractions are artificially propagated distally through the portion of the gastro-intestinal tract.

The period of no stimulation may be of any period or length of time and may be of any period or length of time relative to the period of stimulation. However, in the preferred embodiment, the period of no stimulation is substantially equal to the period of stimulation. Further, the period of stimulation and the equivalent period of no stimulation are selected to provide a period or length of time sufficient to permit the electrical stimulus to produce the local circumferential contractions and to permit the artificial propagation of the contractions through the portion of the gastro-intestinal tract, preferably in a manner facilitating at least a partial emptying thereof.

The period of stimulation is the total length or period of time during which an electrical stimulus is being applied at any of the locations or to any of the electrode sets (24, 26). Thus, in the preferred embodiment, the period of stimulation is equal to the interval of time of application of the electrical stimulus at the proximal location or to the proximal electrode set (24), given that the interval of time of application decreases for each successive location or electrode set (26) and given that the application of the electrical stimuli at all locations or to all electrode sets (24, 26) ceases concurrently.

For example, in the preferred embodiment, if the interval of time of application of the electrical stimulus at the proximal location is 24 seconds, the period of stimulation is 24 seconds. Similarly, the following period of no stimulation is 24 seconds. Thus, a complete cycle, which includes the period of stimulation followed by the period of no stimulation, takes 48 seconds. This cycle is repeated for the length of time necessary to achieve the desired result, preferably at least a partial emptying of the gastro-intestinal tract.

Although the model and the within invention are designed for use with the stomach in the preferred embodiment, as indicated, this invention may also have application to other portions of the gastro-intestinal tract. However, in this case, different electrodes may have to be used due to the thin walls of these tissues.

The within invention is also comprised of a multichannel electrical device (20) that artificially creates and propagates contractions in the gastro-intestinal tract. The device (20) utilizes multi-channel phase-locked stimuli and greater than one set of circumferentially arranged electrodes (24, 26). The device (20) is designed to control the parameters or characteristics of the electrical stimulus (frequency, voltage, wave pattern or configuration) and the propagation pattern (phase-locking, including the length of the time of the application of the stimuli to the electrode set) depending upon the particular requirements of a particular person. Preferably, the device is an implantable microelectronic unit similar to known cardiac pacemakers. Further, preferably, the device (20) is microprocessor-controlled.

Figure 10:
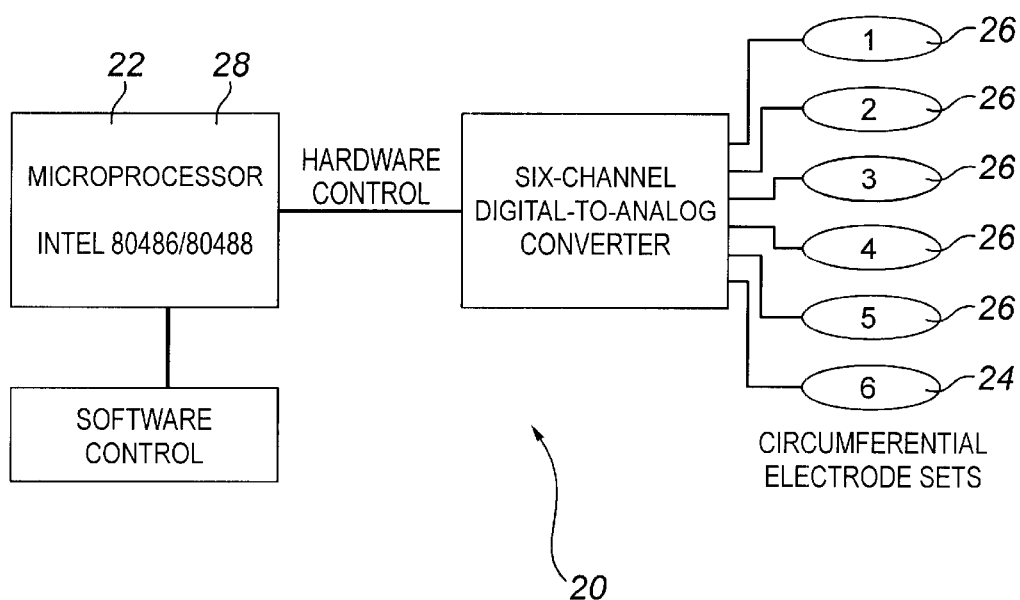
FIG. 10 is a schematic diagram of a preferred embodiment of a microprocessor controlled device of the within invention.

FIG. 10 shows a preferred embodiment of a gastric pacemaker device (20) comprised of a microprocessor for controlling the functioning and operation of the device (20). In this case, the microprocessor may be separate or distinct from the power supply or power source (22) of the device (20). However, preferably, the microprocessor is comprised of the power source (22). In addition, the microprocessor may be separate or distinct from the timing mechanism (28) of the device (20). However, preferably, the microprocessor is comprised of the timing mechanism (28). For instance, the device (20) is preferably comprised of and controlled by specially-designed software on an IBM 486-33 personal computer.

Although microprocessor-based control of the device (20) as shown in FIG. 10 is preferred, the device (20) may alternately utilize discrete electronics to provide the necessary control. For instance, FIGS. 11 and 12 provide an example of an alternate embodiment of a gastric pacemaker device (20), for use in the third study of the inventors as described below, which utilizes discrete electronics to apply the electrical stimuli to produce the artificially propagated contractions in the stomach.

Figure 11:
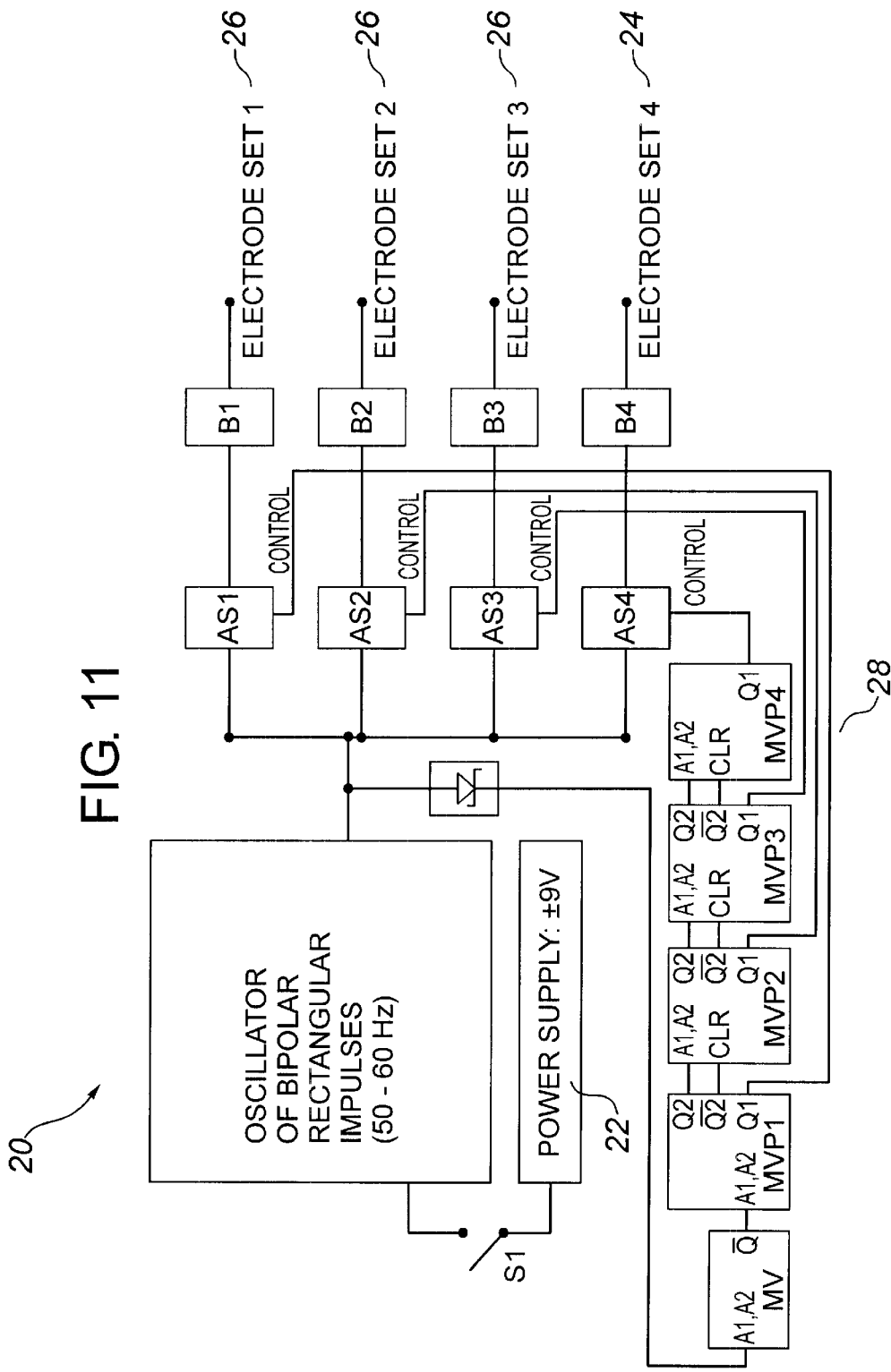
FIG. 11 is a block diagram of an alternate embodiment of the device of the within invention utilizing discrete electronics.
Figure 12:
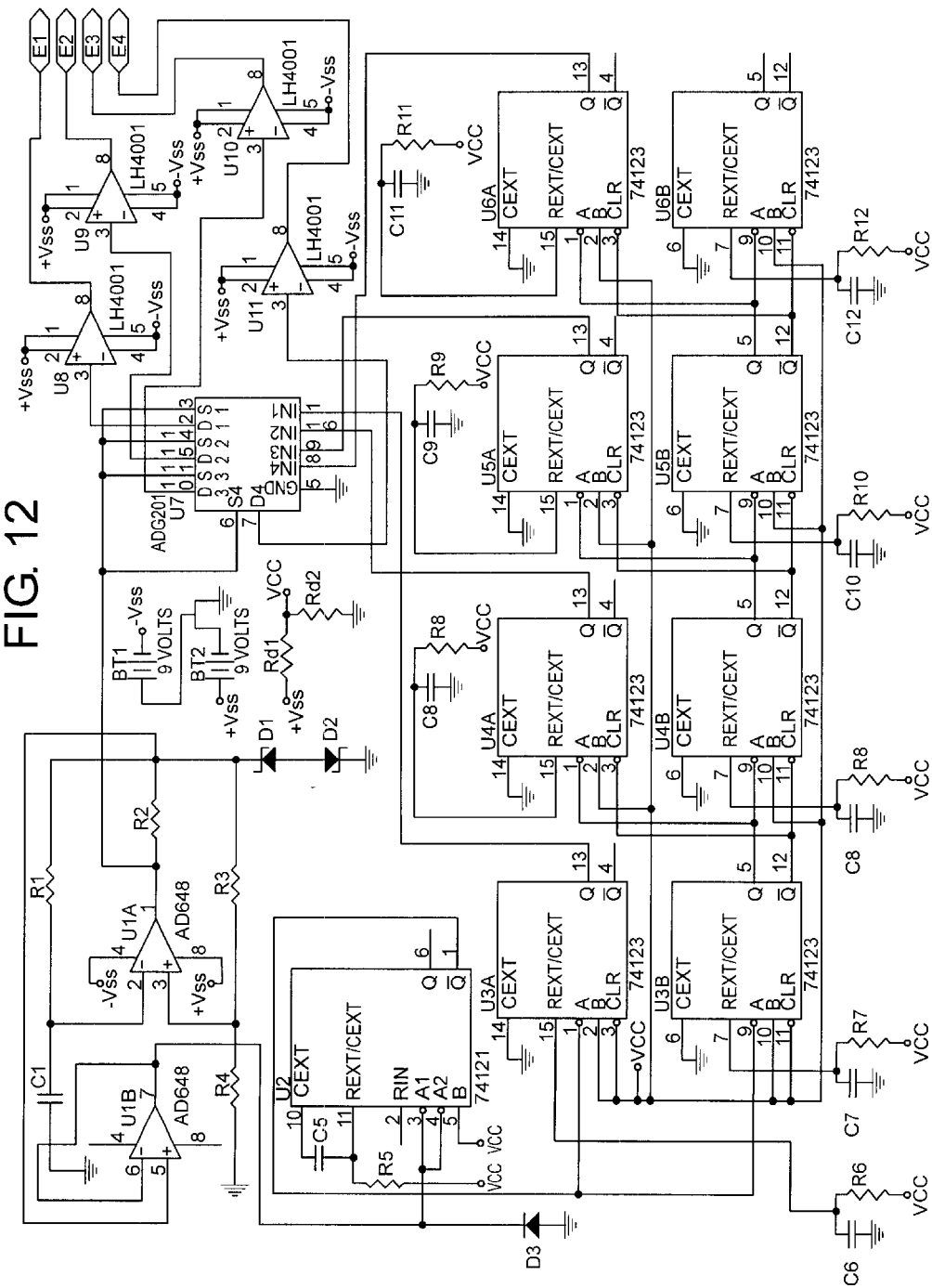
FIG. 12 is a circuit diagram of the device shown in FIG. 11.

Referring to FIGS. 11 and 12, continuous oscillations are produced by a standard electronic oscillator (e.g. astable multivibrator, see IC Op-Amp Cookbook by Walter G. Jung, Howard Sams & Co., Indianapolis, Ind., 1986; ISBN 0-672-22453-4, pp. 461–465).

The start of the oscillations triggers the first pair (MVP 1) of retriggerable monostable multivibrators (e.g. 74LS123, Texas Instruments, Dallas, Tex.). The first of them produces a 2-second impulse which turns on the switch ASI (e.g. ADG201A, Analog Devices, Norwood, Mass.) for 2 seconds thus producing the stimulating voltage train or stimulating interval for the first electrode set (24). At the moment the 2-second impulse for AS1 has started, the inverted output of the second multivibrator initiates a 4-second low-level pulse that is connected to the CLR inputs of the two multivibrators from the second pair, MVP 2, thus blocking both multivibrators from producing any impulses. In the meantime, the first 2-seconds have elapsed, the non-inverting input of the first multivibrator goes back to 0 and the first switch AS1 opens.

Only after the first 4 seconds have elapsed (2 more seconds after the opening of AS1) the first multivibrator from MVP 2, triggered by the first negative slope of the second multivibrator from MVP 1, produces a 2-second impulse which closes the switch AS2 thus producing the stimulating voltage train or stimulating interval for the second electrode set (26). The second multivibrator from MVP 2 is also triggered by the first negative slope of the second multivibrator from MVP 1 and produces a 4-second pulse. Its inverted output is connected to the CLR inputs of the multivibrators from MVP 3. The negative slope of the non-inverted output of MVP 2 triggers MVP 3 and so on. If there are problems with synchronization, all CLR inputs from all multivibrator pairs could be connected to 5 Volts. This interconnection of the controlling multivibrators allows more than 4 electrode sets to be utilized, if necessary. "B" inputs of all multivibrators are connected to high voltage (5 V, obtained from the +9 V battery using a voltage divider).

The work of MVP 1 is controlled by a single multivibrator MV (e.g. 74LS121, Texas Instruments, Dallas, Tex.), which is programmed to produce impulses with a period of 20 seconds, and its output is connected to the CLR inputs of both multivibrators from MVP 1. The "A" inputs of MV are connected to the conditioned output of the oscillator (conditioned so that the amplitude range of the oscillations at the "A" inputs is 0–5 V using, e.g., appropriate zener diodes, a voltage follower and a diode).

The switch S1 turns the stimulator on/off. At the output, 4 analog buffers (LH4001, National Semiconductor, Crawfordsville, Ind.) are preferably used in order to provide the necessary current (in the range of about 5 mA per electrode set).

The application of the within invention and the conoidal model was explored by the inventors in four studies. A first study explored the parameters of the electrical stimulus required to produce a local non-propagated circumferential contraction of the desired portion of the gastro-intestinal tract. A second study explored the phase-locking of the electrical stimulus in order to artificially propagate the local circumferential contractions distally. A third study explored the effect of the application of a first embodiment of a phase-locked electrical stimulus on the emptying of liquids from the portion of the gastro-intestinal tract, while a fourth study explored the effect of the application of the preferred embodiment of a phase-locked electrical stimulus on the emptying of solid food from the portion of the gastrointestinal tract.

In the first study, using two unconscious dogs, two stainless steel wire electrodes (one active, and the other reference or ground) were positioned 3–4 cm apart circumferentially at different locations of the serosal side of the gastric antrum. The electrodes were arranged circumferentially in a plane substantially perpendicular to the longitudinal axis of the stomach. The effect of different stimulating bipolar rectangular voltages on the smooth muscle was examined. The frequency range of the stimulating voltage was 0.005–500 Hz, changed with a step of 10 times (e.g. 0.005 Hz, 0.05 Hz, 0.5 Hz, etc.). Further, 3.0 cc of atropine was subsequently administered intravenously to block the cholinergic nerves and to determine whether the smooth muscle was stimulated directly, or the invoked contraction was a result from stimulating the cholinergic pathways.

When testing the concept of producing local non-propagated contractions on the 2 dogs, low frequency voltages (DC- 0.5 Hz) failed to produce visible contraction regardless of the duration of the applied stimuli. Amplitudes above 5 V (peak-to-peak) were found to be dangerous for the tissue. Whitening of the tissue around the electrodes was noted when stimulating amplitudes were between 5–8 V, and higher amplitudes produced visible burns.

Stimulating voltages of 5, 50 and 500 Hz applied for 2–4 seconds produced quite strong local circumferential non-propagated contractions. Amplitudes up to 20 V did not produce visible damage to the tissue. The response of the smooth muscle to trains of rectangular impulses at 50 Hz (peak-to-peak amplitudes 10–20 V) was found to be preferable and always produced visibly strong local circumferential contraction between and slightly beyond the two stimulating electrodes.

Blocking the cholinergic neurotransmitters with 3.0 cc of atropine, however, abolished or dramatically reduced the significance of the invoked contractions in the whole frequency range of stimulation. The fact that after administering atropine the production of invoked contractions ceased regardless of the stimulating parameters may indicate that the cholinergic pathways were responsible for the invoked contractions. If these pathways are blocked, gastric electrical stimulation to facilitate gastric emptying may not be possible.

Thus, the testing conducted on the 2 dogs suggested that:

(a) the hypothesis that relatively high frequency bipolar voltage can be used for local "in vivo" stimulation of gastric smooth muscle is quite realistic;

(b) the response to stimulation with frequencies higher than 5 Hz is mainly cholinergic in nature and is abolished or significantly suppressed by atropine;

(c) stimulation with a train of 50 Hz rectangular impulses (peak-to-peak amplitude 10–20 V) for about 2–4 seconds can induce almost immediate, relatively strong non-propagated contractions.

Figure 3:
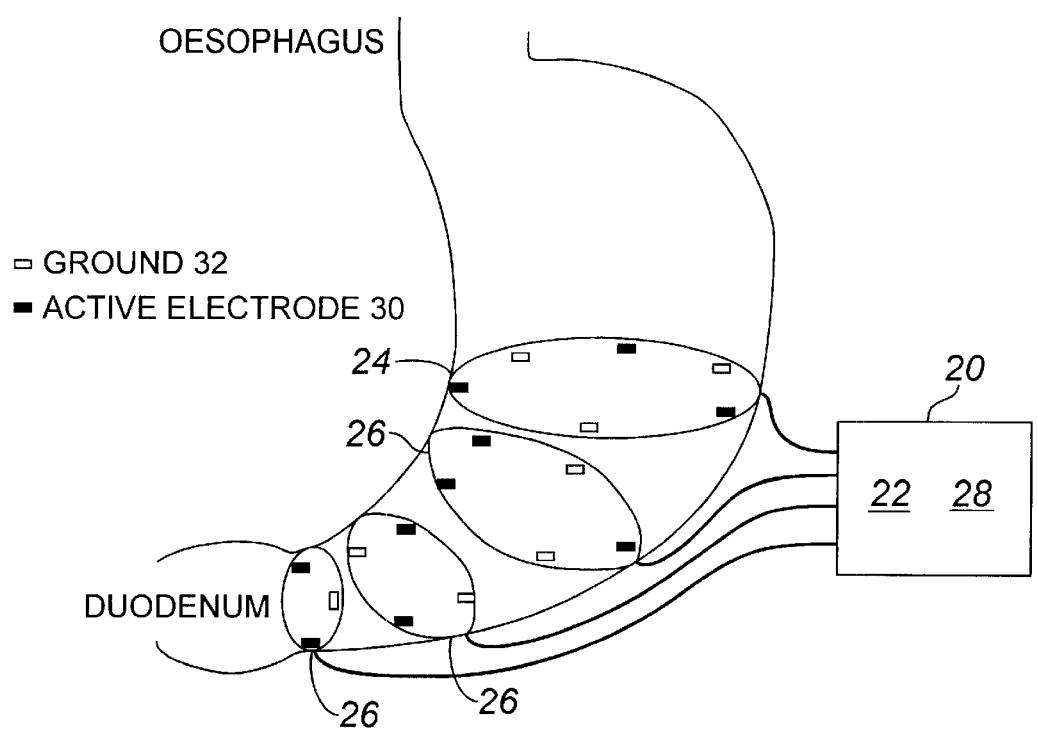
FIG. 3 is a schematic drawing of a canine stomach with 4 sets of circumferentially implanted electrodes in a second study conducted by the inventors.

The second study was conducted to determine if artificially propagated antral contractions could be produced by phase-locking the local circumferential electrical stimulation. In this study, six healthy anaesthetized dogs with similar dimensions (4 female, 2 male, body mass index [weight, kg/height, m] 26.4 ( 2.5 kg/m, weight 29.7 ( 3.8 kg) underwent laparotomy and implantation of pairs of locally designed bipolar stainless steel wire electrodes. Each pair consisted of 2 wires (10×0.25 mm, 3–4 cm apart) implanted subserosally in a circumferential position into the stomach wall. One to 4 electrode pairs were placed at approximately 1, 4.2, 7.8 and 11.7 cm proximally from the pylorus, as shown in FIG. 3. The interelectrode distance in each circumferential set was between 2.5 and 3.5 cm. One of the electrodes from each pair was connected to a common ground.

Figure 4:
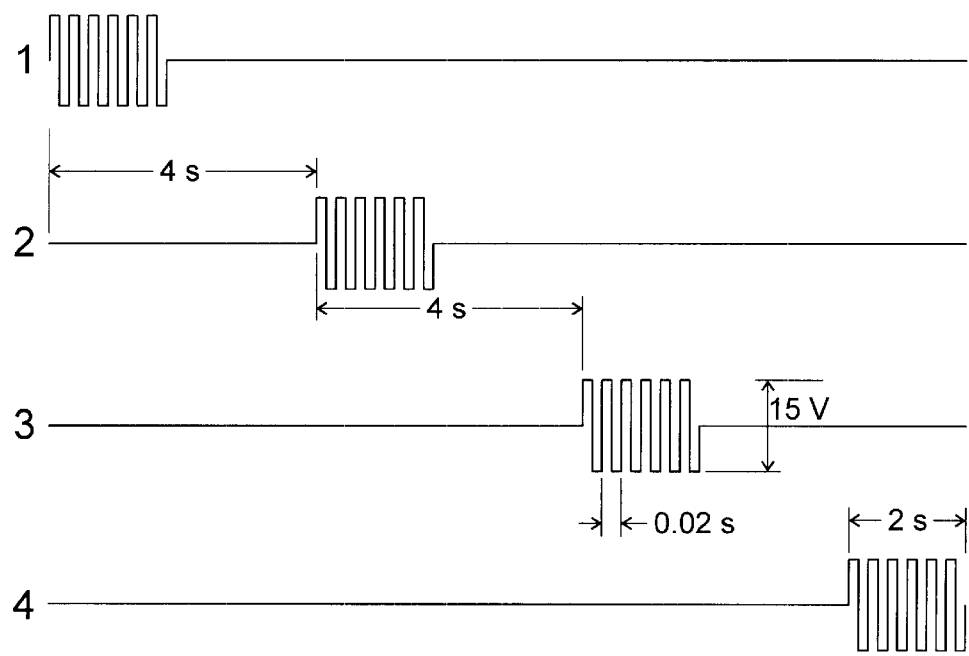
FIG. 4 shows the time characteristics of the stimuli applied to the electrode sets starting with the most proximal as shown in FIG. 3 for the second study.

Computer modeling based on the previously described conoidal dipole model of gastric electrical activity predicted that propagated contractions could be produced circumferentially using at least 4 rings of stimulating electrodes implanted along the gastric circumference and supplied simultaneously with phase-locked bipolar 2-second trains of 50 Hz, 15 V (peak-to-peak) rectangular voltage. These stimulating parameters were applied to the 4 sets of circumferentially-implanted electrodes in the canine antrum, as shown in FIG. 4.

Bipolar voltage stimulation was attempted also at lower (0, 0.005, 0.05, 0.1, 0.2, 0.5, 1, 2, 3, 4, 5, 10, 20, 25, 30 and 40 Hz) and higher (500 Hz) frequencies using various peak-to-peak amplitudes. The stimuli were either phase-locked or independently applied to the individual electrode sets. All electrical stimuli were applied during the estimated resting phase of the migrating myoelectrical complex in the fasting state. The duration of each stimulating session did not exceed 10 minutes.

After testing the effect of various stimuli during the basal state, the cholinergic pathways were blocked with intravenous administration of 3.0 cc of atropine and applied stimulation in the whole frequency/amplitude range for about ½ hour.

Gastric contractions and their propagation are clearly seen in a spontaneously contracting stomach at laparotomy, particularly in the active (third) phase of the migrating myoelectrical complex. Therefore, it was assumed that invoked contractile activity and its propagation (if any) could also be assessed visually during the stimulation sessions. Accordingly, force transducers were not implanted on the serosal wall.

Figure 5:
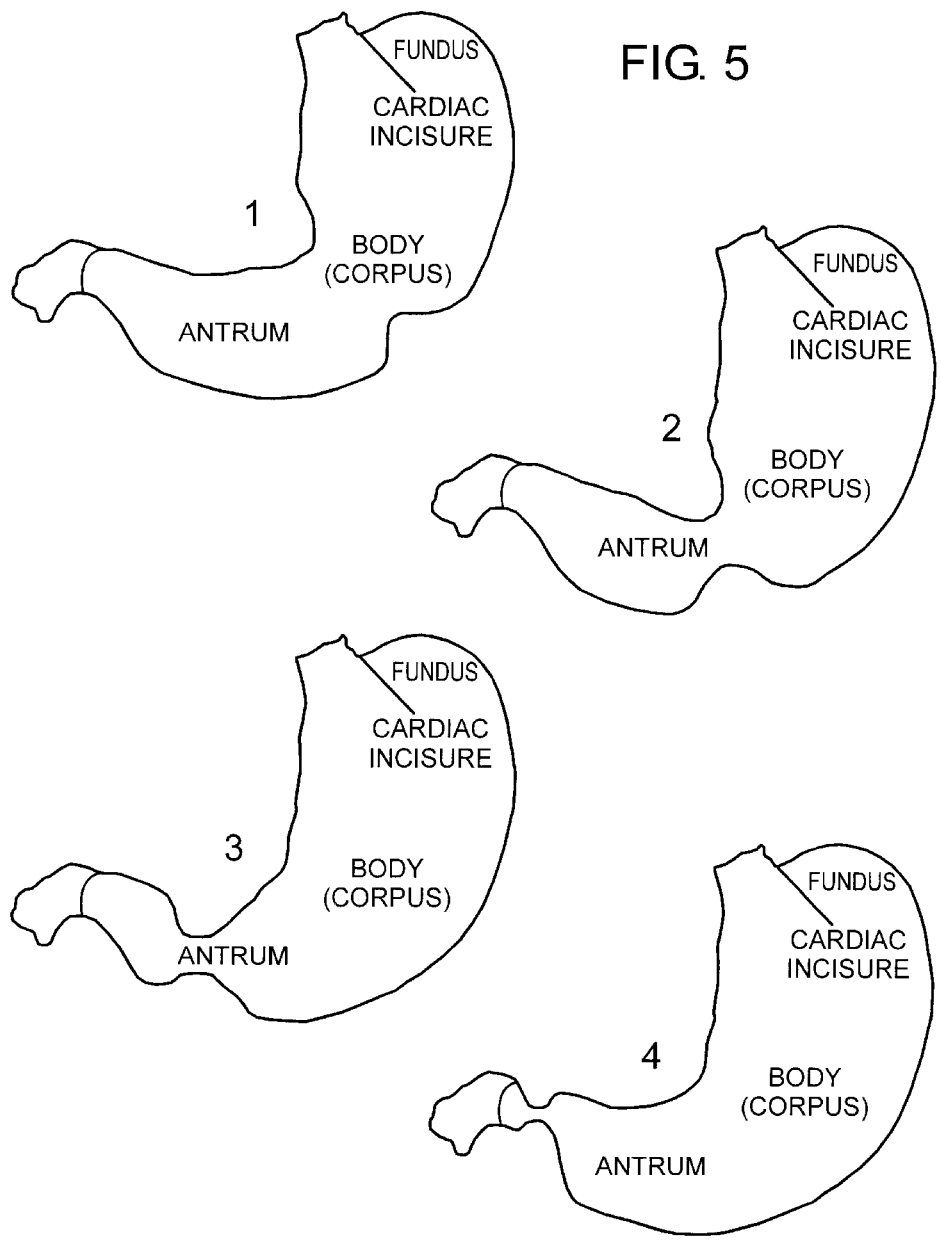
FIG. 5 is a schematic drawing of the 4 artificially invoked contracting phases obtained by phase-locking the stimulating voltage in the electrode sets shown in FIG. 3 for the second study.

Using the parameters suggested by the conoidal computer model, clearly seen gastric contractions were produced which were propagated distally by phase-locking the stimulating voltage, as shown in FIG. 5. Spontaneous propagation of the contractile ring after applying the same stimuli to individual electrode sets was not observed.

When stimulating with 2-second trains of bipolar voltages above 5 Hz and peak-to-peak amplitudes 10–20 V, strong non-propagated circumferential contractions were observed without visible damage to the tissue surrounding the implanted electrodes. These invoked contractions could be artificially propagated from the area of one electrode set to the area of the other by phase-locking the stimulating voltages. The strength of these contractions reached its peak when stimulating at around 50 Hz (providing the peak-to-peak stimulating amplitude was kept the same).

When stimulating with voltages below 5 Hz and a peak-to-peak amplitude range of 10–20 V, visible damage to the tissue around the electrodes was noted which required a reduction in the amplitude of the stimuli and reimplant of the electrodes. Reduction of the peak-to-peak voltage to 5–8 V was associated with whitening of the tissue surrounding the electrodes (the damage to the tissue was milder). No visible contractions were produced after reimplanting the electrodes and reducing the peak-to-peak amplitudes below 5 V.

Stimulation with higher frequency (500 Hz, 10–20 V peak-to-peak) also produced visible circumferential contractions, but they were estimated to be slightly weaker than the contractions produced with stimulating voltage of 50 Hz and the same amplitude range.

Blocking the cholinergic pathways with 3.0 cc of atropine abolished the ability to produce invoked contractions regardless of the frequencies and the amplitudes of the applied stimuli.

As indicated by the second study, stimulating the canine smooth muscle with higher frequencies caused the muscle to respond before the tissue surrounding the implanted electrodes got visibly damaged. The best response was observed at 50 Hz, and peak-to-peak amplitude of 10–20 V seemed to be tolerable. It is possible that the smooth muscle stimulated with bipolar voltage starts to respond to slightly lower stimulating frequencies than when stimulated monopolarly. A circumferential arrangement of the individual electrodes is also preferred, as is the utilization of 4 circumferential electrode sets which are successively positioned in a proximal direction starting from the pyloric region. By phase-locking the applied stimuli between the successive electrode sets (starting this time from the most proximal set) the contraction could be artificially propagated distally.

Figure 6:
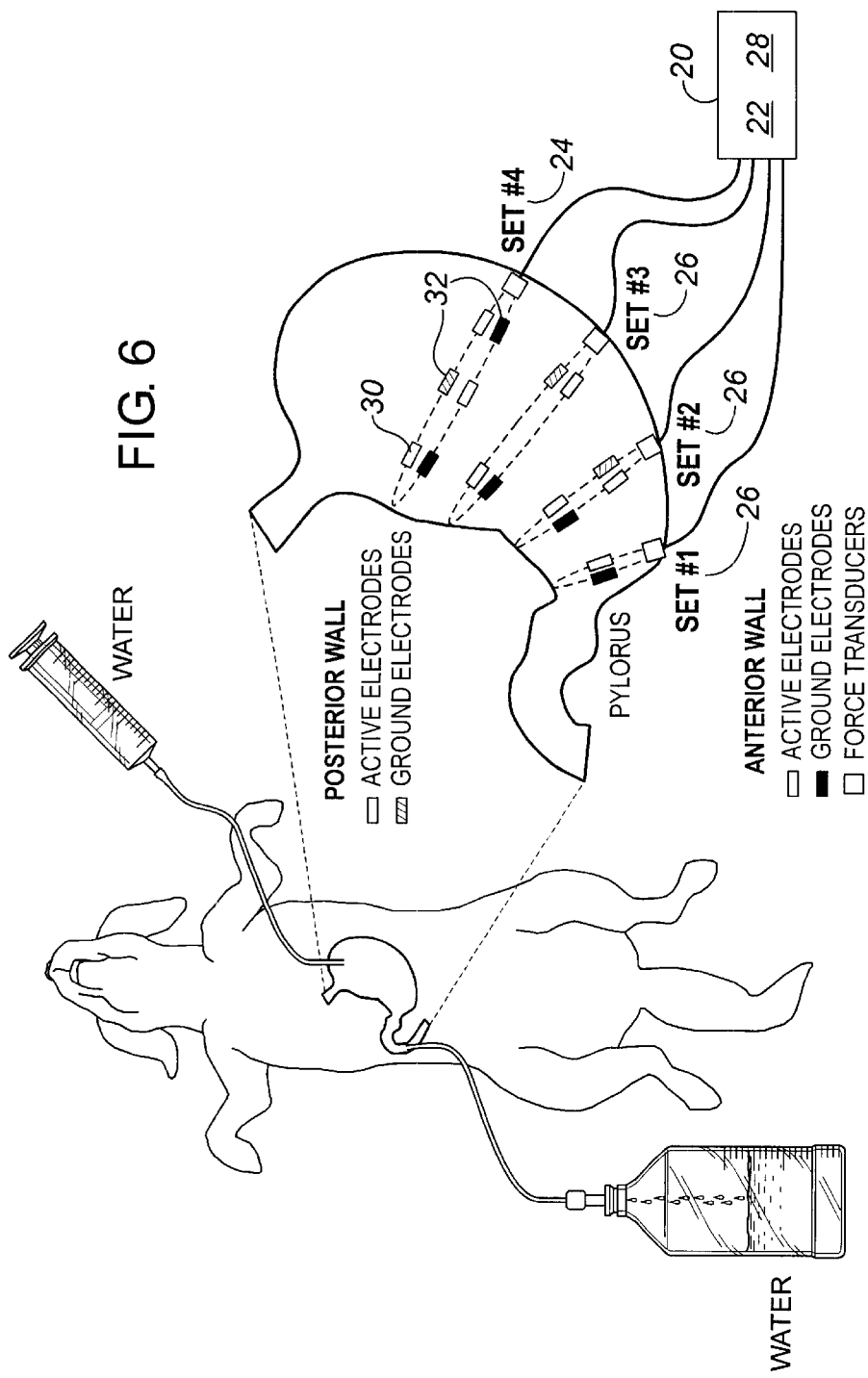
FIG. 6 is a schematic drawing of a canine stomach with 4 sets of circumferentially implanted electrodes in a third study conducted by the inventors.

In the third study, eight healthy anaesthetized dogs with similar dimensions (5 male, 3 female, body mass index [weight, kg/(height, m)$^2$]11.6+/–2.8 kg/m$^2$, weight 18.5+/–3.9 kg) underwent laparotomy and implantation of bipolar stainless steel wire electrodes. Each electrode was a stainless steel wire (10×0.25 mm). Four sets of electrodes were inserted at approximately 2, 6, 10 and 14 cm from the pylorus. Each set consisted of 2 (the most distal set) to 6 electrodes (the most proximal set) inserted under the gastric serosa in a circumferential fashion as shown in FIG. 6. The interelectrode distance in each set was between about 2.5 and 3.5 cm. Every alternate electrode in each electrode set was connected to a common ground. All four sets of wires were connected to a microprocessor-controlled digital stimulator (4-channel 12-bit digital-to-analog converter with up to 6.5 mA current output per channel, controlled by specially designed software on an IBM 486-33 personal computer). In 4 of the dogs, 4 force transducers (RB Products, Madison, Wis.) were implanted close to each circumferential electrode set.

Computer modeling based upon the conoidal model indicated that propagated contractions could be produced circumferentially using 4 rings of stimulating electrodes implanted along the gastric circumference and supplied simultaneously with phase-locked bipolar trains of 50 Hz, 15 V (peak to peak) rectangular voltage and time period between one cycle of the application of the stimulus to all electrode sets and the next cycle of 16 seconds. In this third study, the time period of the cycle of application of the stimulus was increased to 32 seconds and the peak to peak amplitude of the stimulating trains was reduced to 14 V, as shown in FIG. 7.

Figure 9:
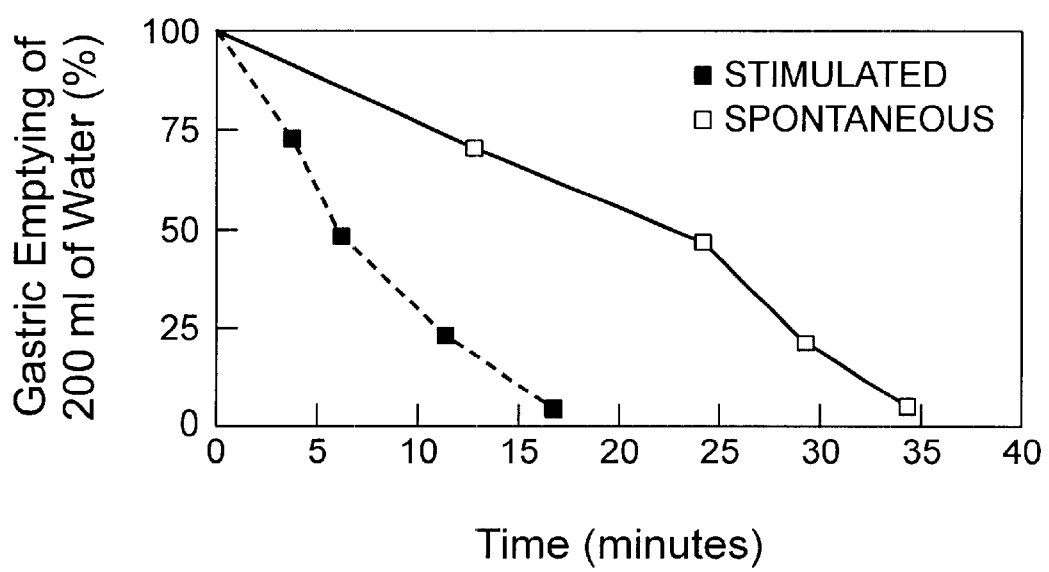
FIG. 9 is a graphical representation of gastric emptying rates with and without electrical stimulation, as shown in FIGS. 6 and 7 for the third study.

Stimulated and spontaneous gastric emptying of liquid contents were compared. A large bore plastic tube (diameter 0.5 cm) was introduced into the apex of the gastric findus in order to fill the stomach with water. Another tube ( diameter 1.5 cm) was positioned in the descending duodenum and the duodenum occluded distal to it. The stomach was filled with 600–800 cc of water. The times to empty 200 ml of water (the estimated amount in the antrum) was compared with and without stimulation. After each emptying session, 200 ml of water were added to the stomach so that the volume of water in the stomach remained the same before each measurement. The tests were repeated at random 3 times per dog. The results for the emptying times were averaged and a single mean value and its standard deviation were obtained for each dog, as set out in FIGS. 8 and 9. The two sets of half-emptying times (T1/2 obtained using stimulation, and through spontaneous emptying) were statistically examined using a standard Chi-square test for significance with the spontaneous emptying mean half-times being the expected values.

Figure 7:
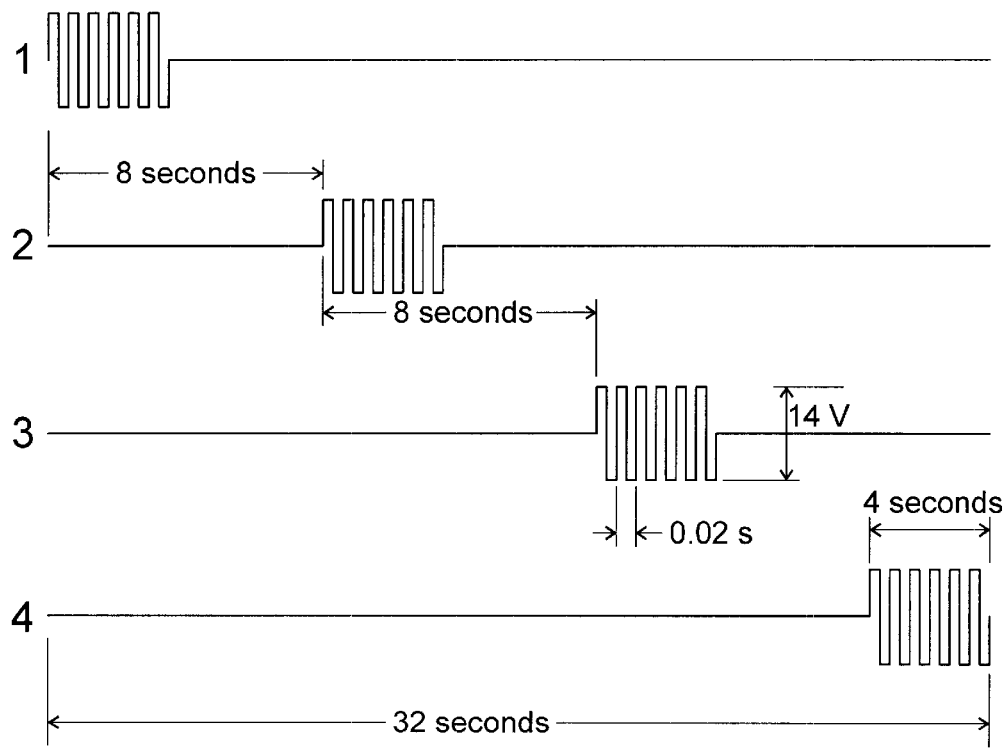
FIG. 7 shows the phase-locking of the electrical stimuli applied to the electrode sets shown in FIG. 6 for the third study.

Using 14 V/50 Hz rectangular trains each having an interval or duration of 4 seconds, followed by an equivalent interval or pause of 4 seconds, as shown in FIG. 7, clearly seen gastric contractions were produced and artificially propagated distally by phase-locking the electrical stimulus. In this third study, the stimulating voltage was phase-locked and the total stimulating current drawn from each electrode set increased gradually in a proximal direction from approximately 1–1.5 mA (for the most distal set) to 6–6.5 mA (for the most proximal set).

The invoked artificially propagated circumferential contractions moved liquid content into the duodenum synchronously with the period of repetition of the stimulating trains. Stimulated mean half-emptying times for each dog were significantly lower than spontaneous mean half-emptying times ($p<0.001$, FIGS. 8 and 9). The averages of overall mean half-times for gastric emptying of water were 25.28+/–12.9 minutes without stimulation and 6.72+/–3.0 minutes with stimulation.

In addition, a test was performed on a 32 year old female patient diagnosed with severe gastroparesis who was undergoing laparotomy and gastrectomy. A set of 4 circumferential electrodes (2 active and 2 grounds) similar to set number 3 shown in FIG. 6 was implanted about 8–10 cm proximal to the pylorus and a stimulating voltage with the characteristics shown in Channel 3 of FIG. 7 was applied. The circumferential electrodes were not implanted permanently and gastric emptying tests were not performed. However, visibly strong circumferential contractions were produced in the stomach of the gastroparetic patient.

In a fourth study of the preferred embodiment of the within invention, the effect of microprocessor-based stimulation techniques on gastric emptying of solid food in an acute dog model was determined. Specifically, nine healthy dogs with similar dimensions (4 male, 5 female, weight 21.5±2.7 kg) underwent laparotomy, and implantation of locally designed bipolar stainless steel wire electrodes pyloroplasty under Penthotal anaesthesia (Abbott, Montreal, Quebec, Canada). The initial dosage of anaesthetic was 30 mg/kg and it was supplemented with 3 mg/kg as needed based on monitoring the restoration of the blinking effect (16). Artificial ventilation was made available during all experiments. At the end of each experiment the animal was sacrificed with an anaesthetic overdose.

Figure 13:
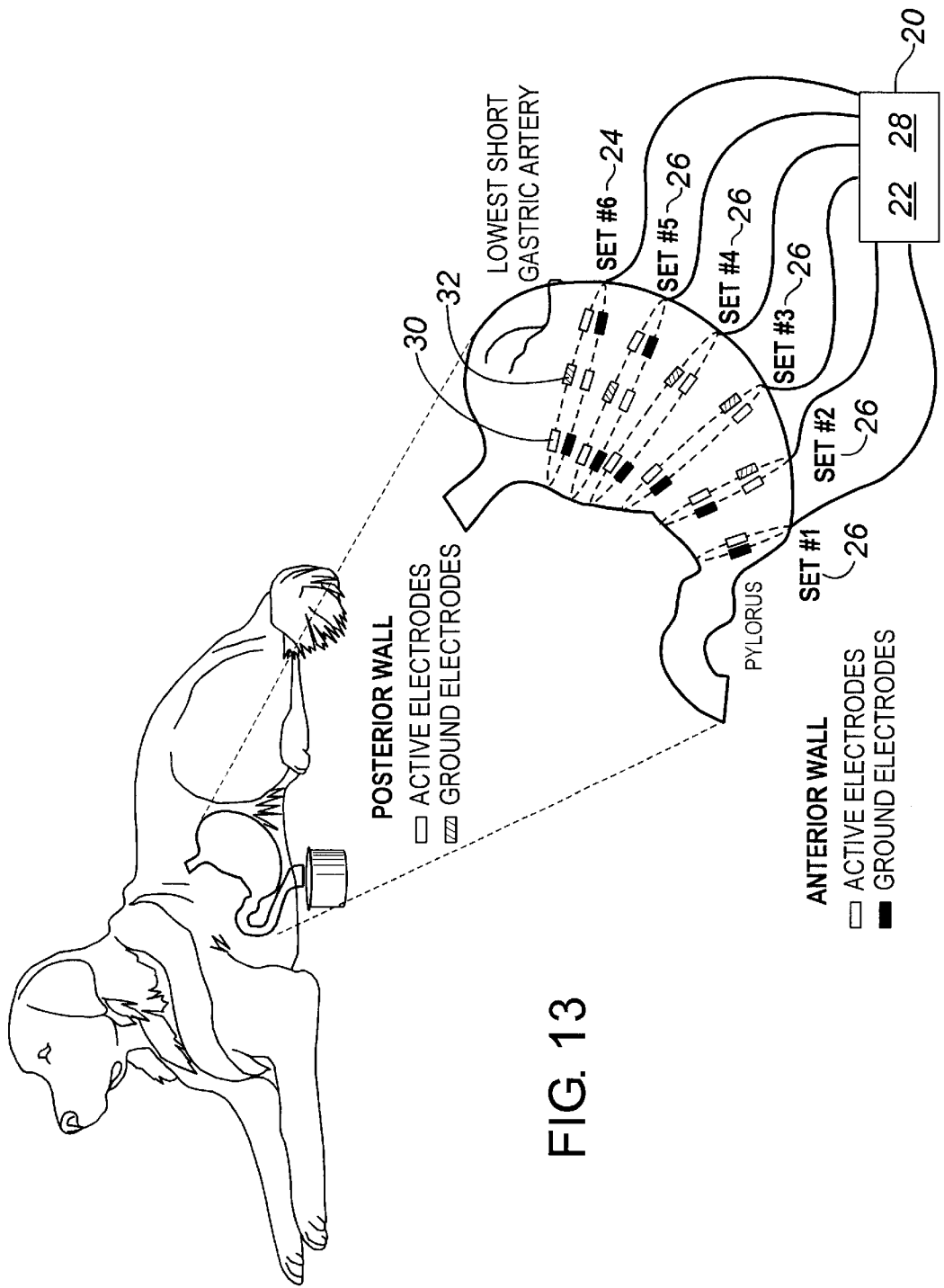
FIG. 13 is a schematic drawing of a canine stomach with 6 sets of circumferentially implanted electrodes in a fourth study conducted by the inventors.

Each implanted electrode was a stainless steel wire (10× 0.25 mm). For instance, as shown in FIG. 13, four to six sets of electrodes were inserted circumferentially at approximately 4 cm intervals measured on the projection of the stomach axis on the anterior gastric wall and starting from the most distal electrode set located at 1.5–2 cm from the pylorus. Each set comprised 2 (the most distal set (26)) to 6 isolated electrode wires (the most proximal set (24)) with 1 cm metal tips. The tips were inserted and sutured subserosally in a circumferential fashion as shown in FIG. 13. The interelectrode distance in each set was between 2.5 and 3.5 cm depending on the gastric circumference in the given location. Every alternative electrode from a given electrode ring was connected to a common ground. All sets of wires were connected to a multichannel microprocessor-controlled digital stimulator (8-channel 12-bit digital to analog converter with up to 6.5 mA current output per channel, controlled by specially designed software on an IBM 486-33 personal computer) as shown in FIG. 10. Further, for the fourth study, the requirements for the Digital-to-Analog Converter were as follows: maximal switching frequency >1 kHz; maximal deliverable voltage output >+/−10V; and maximal deliverable current per channel >6 mA.

Figure 14:
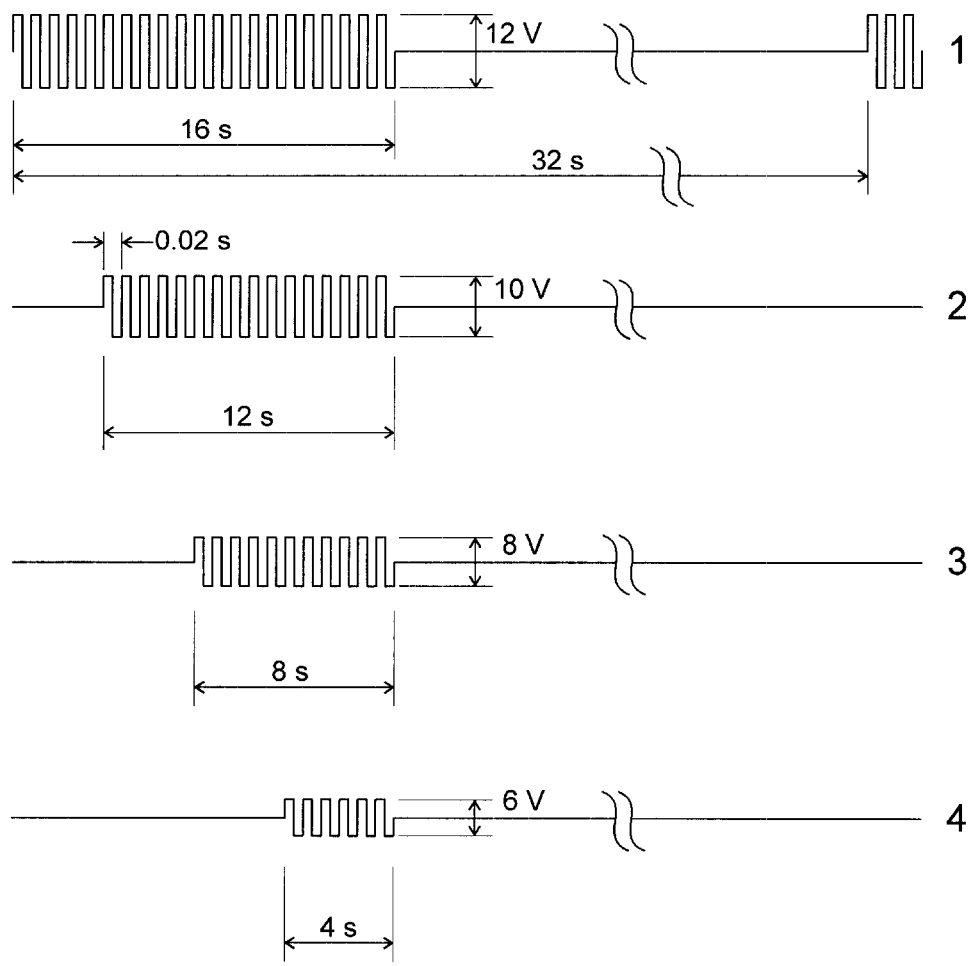
FIG. 14 shows a preferred embodiment of the phase-locking of the electrical stimuli as applied to four sets of circumferentially implanted electrodes.

In the fourth study, a preferred embodiment of an embedded stimuli configuration, having a flexible amplitude of the applied voltages of the electrical stimuli, was used. More particularly, the amplitude of the voltage of each electrical stimulus was decreased in the distal direction and the initial voltage amplitude for the most proximal electrode set (24) was changeable, while the stimulation frequency was maintained at 50 Hz. A preferred embodiment of the phase-locking of the electrical stimuli as applied to six electrode sets is shown in FIG. 14, while a preferred embodiment of the phase-locking of the electrical stimuli as applied to four electrode sets is shown in FIG. 15. A software package was developed for real-time control of the multichannel digital to analog converter using TurboC++ v.3.0 programming language (Borland Inc., Scotts Valley, Calif.).

Stimulated and spontaneous gastric emptying of solid meal content were compared. A large bore plastic tube (diameter 3 cm) was introduced into the apex of the gastric findus in order to fill the stomach with 200 cc of commercially available dog food (Beef Stew, Friskies Petcare, North York, Ontario, Canada) mixed with 40 plastic pellets (cylinders with a radius of 0.75 mm and height of 1.5 mm) (Hythe, Kent, England). Another tube (diameter 3 cm) leading into a plastic dish was positioned in the descending duodenum and the duodenum occluded distal to it.

Figure 17:
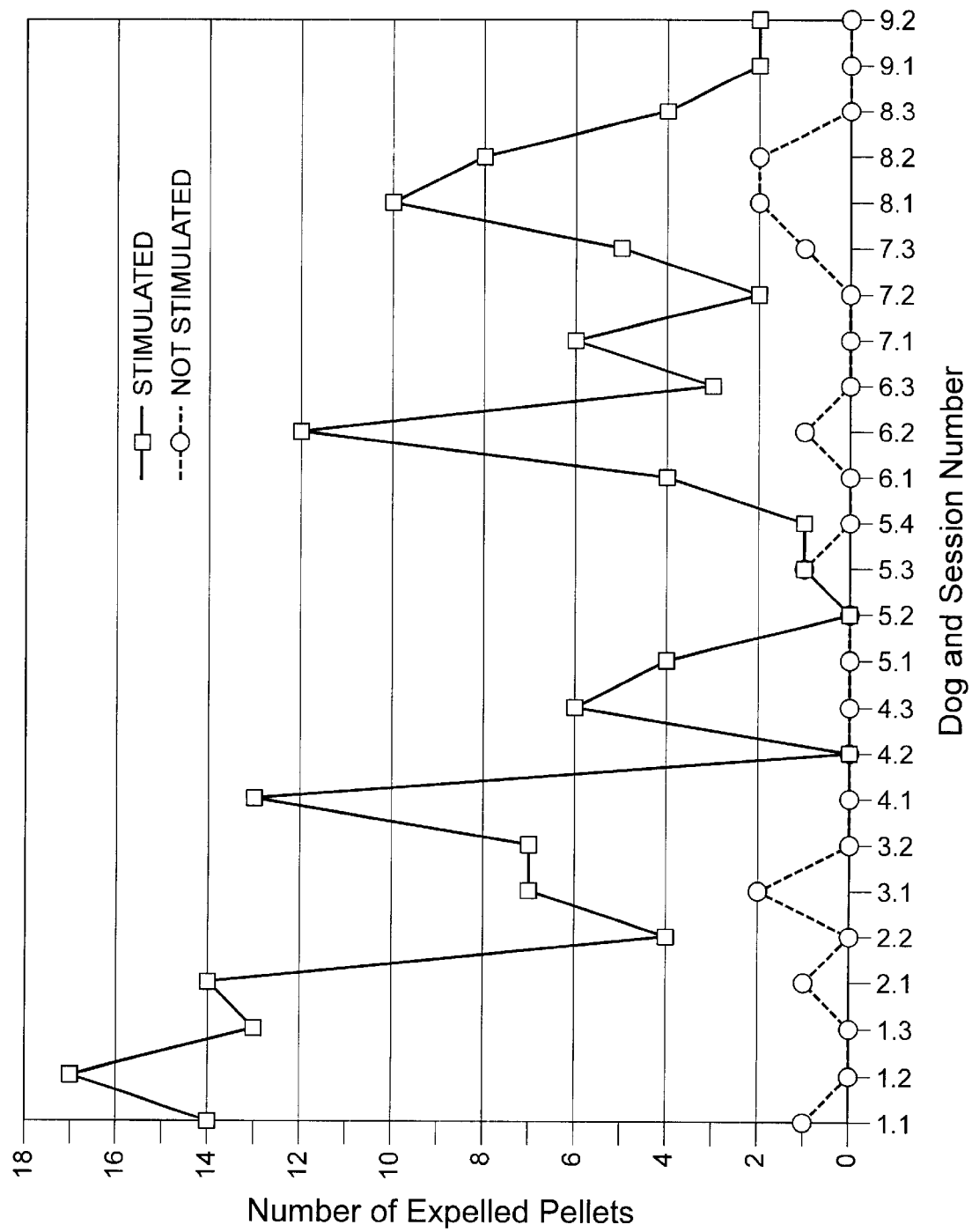
FIG. 17 is a graphical representation showing the effect of the application of the electrical stimuli on the gastric emptying of pellets recorded from one hour gastric emptying sessions for the fourth study conducted by the inventors.

As shown in FIGS. 16 and 17, a comparison was made of the number of pellets expelled into the duodenum with and without stimulation after ½ hour sessions of stimulation-facilitated and spontaneous emptying. After each emptying session the amount of emptied food and pellets were added to the stomach so that the volume of food and the number of pellets in the stomach remained the same before the start of the next session. The two sessions were repeated at random at least 2 times per dog. The number of emptied pellets after each session was documented and statistically examined using a standard Chi-square test for significance with the spontaneous emptying pellet numbers being the expected values.

It was found that the invoked artificially propagated circumferential contractions moved solid food content into the duodenum synchronously with the period or cycle of repetition of the stimulating trains. The number of expelled pellets for each dog after a stimulation session was significantly higher than the number of expelled pellets after spontaneous emptying ($p<0.01$) as shown in FIG. 16. FIG. 17 shows graphically the difference in the gastric emptying rate of pellets in all performed tests.

Further, it was found that using 50 Hz embedded rectangular trains of variable amplitude, clearly seen gastric contractions were able to be produced which were artificially propagated distally by phase locking the electrical stimulus. The duration of these artificial contractions resembled closely the duration of the embedded frequency pulses, with a relaxation time of approximately 3–4 seconds after the termination of the stimulus. The total stimulating current drawn from each electrode set did not exceed 1–1.5 mA (for the most distal set (26)) and 6–6.5 mA (for the most proximal set (24)). The latter number reached the limit of the current-delivery capability of the digital to analog converter of the device (20).

In summary, the fourth study applied microprocessor-controlled sequential neural electrical gastric stimulation ("NEGS") with flexible 50 Hz embedded bipolar rectangular voltage trains and the canine smooth muscle responded with strong contractions without visible damage of the tissue surrounding the implanted electrodes. This voltage stimulation approach may be regarded as a rough recreation of the natural gastric "microprocessor". It is believed that this type of stimulation is largely mediated through cholinergic neural pathways.

By phase locking the applied embedded electrical stimuli between the successive electrode sets (starting from the most proximal set (24)), the contraction was artificially propagated distally while diminishing retrograde propagation of content. This artificial propagation of the contraction is preferably controlled by a microprocessor. The flexibility of and control over the phase locking of the electrical stimuli, including the stimulation and synchronization patterns, and of the durations of the period of stimulation and period of no stimulation make the within device (20) and methods easily adjustable to different patterns of stimulation and rates of gastric emptying that might be needed in patients in various stages of gastroparesis, or/and with various gastric dimensions.

The embodiments of the invention in which an exclusive privilege or property is claimed are defined as follows:

1. A device for electrical stimulation of smooth muscle comprising a portion of the gastro-intestinal tract, wherein the portion of the gastro-intestinal tract defines a longitudinal axis extending therethrough, the device comprising:

(a) a proximal electrode set for arrangement circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;

(b) at least one distal electrode set for arrangement circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;

(c) at least one power source for providing a variable electrical stimulus to the proximal and distal electrode sets sufficient to stimulate the smooth muscle to produce the local circumferential contractions, wherein the electrical stimulus is variable between each of the proximal and distal electrode sets;

(d) a timing mechanism, associated with the power source, for phase locking the electrical stimulus such that the electrical stimulus is applied to the proximal and distal electrode sets successively and repetitively, wherein the timing mechanism applies the electrical stimulus to each electrode set for an interval of time in overlapping succession such that the application of the electrical stimulus to each electrode set ceases following the commencement of the application of the electrical stimulus to the next successive electrode set;

wherein the axially spaced relationship between the electrode sets and the timing of the electrical stimulus applied to the electrode sets are selected such that the local circumferential contractions are artificially propagated distally through the portion of the gastro-intestinal tract.

2. The device as claimed in claim 1 wherein the interval of time of application of the electrical stimulus to each electrode set is variable between successive electrode sets.

3. The device as claimed in claim 2 wherein the interval of time of application of the electrical stimulus to each electrode set decreases with each successive electrode set.

4. The device as claimed in claim 3 wherein the application of the electrical stimulus to each proximal and distal electrode sets ceases substantially concurrently.

5. A method for electrical stimulation of smooth muscle comprising a portion of the gastro-intestinal tract, wherein the portion of the gastro-intestinal tract defines a longitudinal axis extending therethrough and wherein the method is performed using a device comprised of a proximal electrode set and at least one distal electrode set, the method comprising the steps of:

(a) arranging the proximal electrode set circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;

(b) arranging each of the distal electrode sets circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;

(c) applying a variable electrical stimulus to the proximal and distal electrode sets sufficient to stimulate the smooth muscle to produce the local circumferential contractions, wherein the electrical stimulus is variable between each of the proximal and distal electrode sets, wherein the electrical stimulus is phase-locked such that the electrical stimulus is applied to the proximal and distal electrode sets successively and repetitively and wherein the applying step is comprised of applying the electrical stimulus to each electrode set for an interval of time in overlapping succession such that the application of the electrical stimulus to each electrode set ceases following the commencement of the application of the electrical stimulus to the next successive electrode set;

wherein the axially spaced relationship between the electrode sets and the timing of the phase-locking of the electrical stimulus applied to the electrode sets are selected such that the local circumferential contractions are artificially propagated distally through the portion of the gastro-intestinal tract.

6. The method as claimed in claim 5 wherein the interval of time of application of the electrical stimulus to each electrode set is variable between successive electrode sets.

7. The method as claimed in claim 6 wherein the interval of time of application of the electrical stimulus to each electrode set decreases with each successive electrode set.

8. The method as claimed in claim 7 wherein the application of the electrical stimulus to each proximal and distal electrode sets ceases substantially concurrently.

9. The method as claimed in claim 6 wherein the electrical stimulus applied to the proximal and distal electrode sets is alternating.

10. The method as claimed in claim 9 wherein the alternating electrical stimulus is bipolar.

11. The method as claimed in claim 10 wherein the shape of the alternating electrical stimulus is rectangular or square.

12. The method as claimed in claim 11 wherein the frequency of the alternating electrical stimulus is between about 5 to 500 Hertz and wherein the frequency of the alternating electrical stimulus is variable between each of the proximal and distal electrode sets.

13. The method as claimed in claim 12 wherein the frequency of the alternating electrical stimulus is between about 5 to 50 Hertz.

14. The method as claimed in claim 13 wherein the frequency of the alternating electrical stimulus is about 50 Hertz.

15. The method as claimed in claim 14 wherein the voltage of the alternating electrical stimulus is less than or equal to about 20 Volts, peak to peak, and wherein the applying step is comprised of varying the voltage of the alternating electrical stimulus between each of the proximal and distal electrode sets.

16. The method as claimed in claim 15 wherein the voltage of the alternating electrical stimulus is less than or equal to about 15 Volts, peak to peak, and wherein the applying step is comprised of decreasing the voltage of the alternating electrical stimulus applied to each successive electrode set.

17. The method as claimed in claim 16 wherein the voltage of the alternating electrical stimulus is between about 4 to 14 Volts, peak to peak.

18. The method as claimed in claim 17 wherein the applying step is comprised of applying the electrical stimulus to each successive electrode set for an interval of time of less than or equal to about 24 seconds.

19. The method as claimed in claim 18 wherein the interval of time is between about 4 to 24 seconds.

20. A method for electrical stimulation of smooth muscle comprising a portion of the gastro-intestinal tract, wherein the portion of the gastro-intestinal tract defines a longitudinal axis extending therethrough, the method comprising the steps of:

(a) applying an electrical stimulus at a proximal location to the smooth muscle circumferentially about the portion of the gastro-intestinal tract in a plane substantially perpendicular to the longitudinal axis, wherein the electrical stimulus is sufficient to stimulate the smooth muscle to produce a local circumferential contraction at the proximal location;

(b) applying an electrical stimulus at at least one distal location to the smooth muscle circumferentially about the portion of the gastro-intestinal tract in a plane substantially perpendicular to the longitudinal axis, wherein the distal location is in axially spaced relationship relative to the proximal location, wherein the electrical stimulus is sufficient to stimulate the smooth muscle to produce a local circumferential contraction at the distal location and wherein the applied electrical stimulus is varied between each of the proximal and distal locations; and (c) phase-locking the electrical stimulus applied at the proximal and distal locations such that the electrical stimulus is applied at the proximal and distal locations successively and repetitively, wherein the phase-locking step is comprised of applying the electrical stimulus at each location for an interval of time in overlapping succession such that the application of the electrical stimulus at each location ceases following the commencement of the application of the electrical stimulus at the next successive location;

wherein the axially spaced relationship between the proximal and distal locations and the timing of the phase-locking of the electrical stimulus applied to the locations are selected such that the local circumferential contractions are artificially propagated distally through the portion of the gastro-intestinal tract.

21. The method as claimed in claim 20 wherein the interval of time of application of the electrical stimulus at each proximal and distal location is variable between successive locations.

22. The method as claimed in claim 21 wherein the interval of time of application of the electrical stimulus at each location decreases with each successive location.

23. The method as claimed in claim 22 wherein the application of the electrical stimulus at each proximal and distal location ceases substantially concurrently.

24. A device for electrical stimulation of smooth muscle comprising a portion of the gastro-intestinal tract, wherein the portion of the gastro-intestinal tract defines a longitudinal axis extending therethrough, the device comprising:

(a) a proximal electrode set for arrangement circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;

(b) at least one distal electrode set for arrangement circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;

(c) at least one power source for providing a variable electrical stimulus to the proximal and distal electrode sets sufficient to stimulate the smooth muscle to produce the local circumferential contractions, wherein the electrical stimulus is variable between each of the proximal and distal electrode sets;

(d) a timing mechanism, associated with the power source, for phase locking the electrical stimulus such that the electrical stimulus is applied to the proximal and distal electrode sets successively and repetitively, wherein the timing mechanism applies the electrical stimulus to each electrode set for an interval of time in overlapping succession such that the application of the electrical stimulus to each electrode set ceases following the commencement of the application of the electrical stimulus to all successive electrode sets;

wherein the axially spaced relationship between the electrode sets and the timing of the electrical stimulus applied to the electrode sets are selected such that the local circumferential contractions are artificially propagated distally through the portion of the gastro-intestinal tract.

25. The device as claimed in claim 24 wherein the application of the electrical stimulus to each proximal and distal electrode sets ceases substantially concurrently.

26. The device as claimed in claim 25 wherein the timing mechanism applies the electrical stimulus to the proximal and distal electrode sets such that the electrical stimulus is applied to the proximal and distal electrode sets in succession for a period of stimulation, following which there is a period of no stimulation before the next application of the electrical stimulus to the proximal and distal electrode sets.

27. The device as claimed in claim 26 wherein the period of no stimulation is substantially equal to the period of stimulation.

28. The device as claimed in claim 26 wherein the portion of the gastro-intestinal tract is comprised of the esophagus, the stomach, the small intestine, the large intestine, the anal sphincter and combinations thereof.

29. The device as claimed in claim 28 wherein the portion of the gastro-intestinal tract is comprised of the stomach.

30. The device as claimed in claim 29 comprising at least three distal electrode sets for arrangement circumferentially about the portion of the gastro-intestinal tract distally to the proximal electrode set and in an axially spaced relationship with each other such that the phase-locked electrical stimulus produces a local circumferential contraction at the proximal electrode set and each distal electrode set in succession.

31. The device as claimed in claim 30 wherein the artificial propagation of local contractions through the stomach is sufficient to facilitate at least a partial emptying thereof.

32. The device as claimed in claim 31 wherein the proximal electrode set is for arrangement circumferentially about the mid-corpus of the stomach.

33. The device as claimed in claim 32 wherein each of the proximal and distal electrode sets is comprised of at least one active electrode and at least one ground electrode, wherein the active electrodes are connected to the power source in a manner such that the electrical stimulus is provided concurrently to each of the active electrodes included in an electrode set.

34. The device as claimed in claim 33 wherein the number of active electrodes is greater than or equal to the number of ground electrodes in each of the proximal and distal electrode sets.

35. The device as claimed in claim 33 wherein the electrical stimulus is provided by an alternating voltage source.

36. The device as claimed in claim 35 wherein the alternating voltage source is a bipolar alternating voltage source.

37. The device as claimed in claim 36 wherein the alternating voltage source is a rectangular alternating voltage source or a square alternating voltage source.

38. The device as claimed in claim 37 wherein the frequency of the alternating voltage source is between about 5 to 500 Hertz and wherein the frequency of the alternating voltage source is variable between each of the proximal and distal electrode sets.

39. The device as claimed in claim 38 wherein the frequency of the alternating voltage source is between about 5 to 50 Hertz.

40. The device as claimed in claim 39 wherein the frequency of the alternating voltage source is about 50 Hertz.

41. The device as claimed in claim 40 wherein the voltage provided by the alternating voltage source is less than or equal to about 20 Volts, peak to peak, and wherein the voltage of the alternating voltage source is variable between each of the proximal and distal electrode sets.

42. The device as claimed in claim 41 wherein the voltage provided by the alternating voltage source is less than or equal to about 15 Volts, peak to peak.

43. The device as claimed in claim 42 wherein the voltage provided by the alternating voltage source is between about 4 to 14 Volts, peak to peak.

44. The device as claimed in claim 43 wherein the interval of time of the application of the electrical stimulus to each proximal and distal electrode set is less than or equal to about 24 seconds.

45. The device as claimed in claim 44 wherein the interval of time is between about 4 to 24 seconds.

46. A method for electrical stimulation of smooth muscle comprising a portion of the gastro-intestinal tract, wherein the portion of the gastro-intestinal tract defines a longitudinal axis extending therethrough and wherein the method is performed using a device comprised of a proximal electrode set and at least one distal electrode set, the method comprising the steps of:
   (a) arranging the proximal electrode set circumferentially about the portion of the gastro-intestinal tract in a plane substantially perpendicular to the longitudinal axis such that the smooth muscle may be stimulated thereby to produce a local circumferential contraction of the smooth muscle at the location of the proximal electrode set;
   (b) arranging each of the distal electrode sets circumferentially about the portion of the gastro-intestinal tract in a plane substantially perpendicular to the longitudinal axis and in axially spaced relationship relative to the proximal electrode set such that the smooth muscle may be stimulated thereby to produce a local circumferential contraction of the smooth muscle at the location of the distal electrode set;
   (c) applying a variable electrical stimulus to the proximal and distal electrode sets sufficient to stimulate the smooth muscle to produce the local circumferential contractions, wherein the electrical stimulus is variable between each of the proximal and distal electrode sets, wherein the electrical stimulus is phase-locked such that the electrical stimulus is applied to the proximal and distal electrode sets successively and repetitively and wherein the applying step is comprised of applying the electrical stimulus to each electrode set for an interval of time in overlapping succession such that the application of the electrical stimulus to each electrode set ceases following the commencement of the application of the electrical stimulus to all successive electrode sets;
wherein the axially spaced relationship between the electrode sets and the timing of the phase-locking of the electrical stimulus applied to the electrode sets are selected such that the local circumferential contractions are artificially propagated distally through the portion of the gastro-intestinal tract.

47. The method as claimed in claim 46 wherein the application of the electrical stimulus to each proximal and distal electrode sets ceases substantially concurrently.

48. The method as claimed in claim 47 wherein the applying step is comprised of applying the electrical stimulus to the proximal and distal electrode sets such that the electrical stimulus is applied to the proximal and distal electrode sets in succession for a period of stimulation, following which there is a period of no stimulation before the next application of the electrical stimulus to the proximal and distal electrode sets.

49. The method as claimed in claim 48 wherein the period of no stimulation is substantially equal to the period of stimulation.

50. The method as claimed in claim 48 wherein the portion of the gastro-intestinal tract is comprised of the esophagus, the stomach, the small intestine, the large intestine, the anal sphincter and combinations thereof.

51. The method as claimed in claim 50 wherein the portion of the gastro-intestinal tract is comprised of the stomach.

52. The method as claimed in claim 51 wherein the proximal and distal electrode sets are implanted subserosally in the stomach.

53. The method as claimed in claim 51 wherein the device is comprised of at least three distal electrode sets and wherein the distal electrode sets are arranged distally to the proximal electrode set and in an axially spaced relationship with each other such that the phase-locked electrical stimulus produces a local circumferential contraction at the proximal electrode set and at each distal electrode set in succession.

54. The method as claimed in claim 53 wherein the artificial propagation of local contractions through the stomach is sufficient to facilitate at least a partial emptying thereof.

55. The method as claimed in claim 54 wherein the proximal electrode set is arranged in about the mid-corpus of the stomach.

56. A method for electrical stimulation of smooth muscle comprising a portion of the gastro-intestinal tract, wherein the portion of the gastro-intestinal tract defines a longitudinal axis extending therethrough, the method comprising the steps of:
   (a) applying an electrical stimulus at a proximal location to the smooth muscle circumferentially about the portion of the gastro-intestinal tract in a plane substantially perpendicular to the longitudinal axis, wherein the electrical stimulus is sufficient to stimulate the smooth muscle to produce a local circumferential contraction at the proximal location;
   (b) applying an electrical stimulus at at least one distal location to the smooth muscle circumferentially about the portion of the gastro-intestinal tract in a plane substantially perpendicular to the longitudinal axis, wherein the distal location is in axially spaced relationship relative to the proximal location, wherein the electrical stimulus is sufficient to stimulate the smooth muscle to produce a local circumferential contraction at the distal location and wherein the applied electrical stimulus is varied between each of the proximal and distal locations; and
   (c) phase-locking the electrical stimulus applied at the proximal and distal locations such that the electrical stimulus is applied at the proximal and distal locations successively and repetitively, wherein the phase-locking step is comprised of applying the electrical stimulus at each location for an interval of time in overlapping succession such that the application of the electrical stimulus at each location ceases following the commencement of the application of the electrical stimulus at all successive locations;

wherein the axially spaced relationship between the proximal and distal locations and the timing of the phase-locking of the electrical stimulus applied to the locations are selected such that the local circumferential contractions are artificially propagated distally through the portion of the gastro-intestinal tract.

57. The method as claimed in claim 56 wherein the application of the electrical stimulus at each proximal and distal location ceases substantially concurrently.

58. The method as claimed in claim 57 wherein the phase-locking step is comprised of applying the electrical stimulus at the proximal and distal locations such that the electrical stimulus is applied at the proximal and distal locations in succession for a period of stimulation, following which there is a period of no stimulation before the next application of the electrical stimulus at the proximal and distal locations.

59. The method as claimed in claim 58 wherein the period of no stimulation is substantially equal to the period of stimulation.

60. The method as claimed in claim 58 wherein the portion of the gastro-intestinal tract is comprised of the esophagus, the stomach, the small intestine, the large intestine, the anal sphincter and combinations thereof.

61. The method as claimed in claim 60 wherein the portion of the gastro-intestinal tract is comprised of the stomach.

62. The method as claimed in claim 61 wherein the electrical stimulus is applied at the proximal and distal locations subserosally in the stomach.

63. The method as claimed in claim 62 wherein the electrical stimulus is applied at at least three distal locations and wherein the distal locations are located distally to the proximal location and in an axially spaced relationship with each other such that the phase-locking of the electrical stimulus produces a local circumferential contraction at the proximal location and each distal location in succession.

64. The method as claimed in claim 63 wherein the artificial propagation of local contractions through the stomach is sufficient to facilitate at least a partial emptying thereof.

65. The method as claimed in claim 64 wherein the proximal location is located in about the mid-corpus of the stomach.

66. The method as claimed in claim 65 wherein the electrical stimulus applied at the proximal and distal locations is alternating.

67. The method as claimed in claim 66 wherein the alternating electrical stimulus is bipolar.

68. The method as claimed in claim 67 wherein the shape of the alternating electrical stimulus is rectangular or square.

69. The method as claimed in claim 68 wherein the frequency of the alternating electrical stimulus is between about 5 to 500 Hertz and wherein the frequency of the alternating electrical stimulus is variable between each of the proximal and distal locations.

70. The method as claimed in claim 69 wherein the frequency of the alternating electrical stimulus is between about 5 to 50 Hertz.

71. The method as claimed in claim 70 wherein the frequency of the alternating electrical stimulus is about 50 Hertz.

72. The method as claimed in claim 71 wherein the voltage of the alternating electrical stimulus is less than or equal to about 20 Volts, peak to peak, and wherein the voltage of the alternating electrical stimulus applied at the proximal location varies from the voltage of the alternating electrical stimulus applied at each successive distal location.

73. The method as claimed in claim 72 wherein the voltage of the alternating electrical stimulus is less than or equal to about 15 Volts, peak to peak, and wherein a decreasing voltage is applied at each successive location.

74. The method as claimed in claim 73 wherein the voltage of the alternating electrical stimulus is between about 4 to 14 Volts, peak to peak.

75. The method as claimed in claim 74 wherein the phase-locking step is comprised of applying the electrical stimulus at each successive location for an interval of time of less than or equal to about 24 seconds.

76. The method as claimed in claim 75 wherein the interval of time is between about 4 to 24 seconds.

* * * * *

UNITED STATES PATENT AND TRADEMARK OFFICE
CERTIFICATE OF CORRECTION

PATENT NO.     : 6,449,511 B1
DATED          : September 10, 2002
INVENTOR(S)    : Martin P. Mintchev and Kenneth L. Bowes It is certified that error appears in the above-identified patent and that said Letters Patent is hereby corrected as shown below:

Column 18,
Line 31, after "Distances", change "cm" to -- (cm) --

Column 22,
Line 33, change "ASI" to -- AS1 --

Column 23,
Line 48, change "bums" to -- burns --

Signed and Sealed this

Fourth Day of March, 2003

JAMES E. ROGAN
*Director of the United States Patent and Trademark Office*